(12) United States Patent
Wai

(10) Patent No.: US 7,399,763 B2
(45) Date of Patent: Jul. 15, 2008

(54) 8-HYDROXY-1-OXO-TETRAHYDROPYRROLO-PYRAZINE COMPOUNDS USEFUL AS HIV INTEGRASE INHIBITORS

(75) Inventor: John S. Wai, Harleysville, PA (US)

(73) Assignee: Merck & Co., Inc., Rahway, NJ (US)

( * ) Notice: Subject to any disclaimer, the term of this patent is extended or adjusted under 35 U.S.C. 154(b) by 576 days.

(21) Appl. No.: 10/526,280

(22) PCT Filed: Sep. 10, 2003

(86) PCT No.: PCT/US03/28363

§ 371 (c)(1),
(2), (4) Date: Mar. 1, 2005

(87) PCT Pub. No.: WO2004/047725

PCT Pub. Date: Jun. 10, 2004

(65) Prior Publication Data

US 2005/0288293 A1    Dec. 29, 2005

Related U.S. Application Data

(60) Provisional application No. 60/409,745, filed on Sep. 11, 2002.

(51) Int. Cl.
C07D 241/36 (2006.01)
A61K 31/498 (2006.01)

(52) U.S. Cl. .................... 514/249; 544/349

(58) Field of Classification Search .............. 544/349; 514/249
See application file for complete search history.

(56) References Cited

U.S. PATENT DOCUMENTS

| | | | |
|---|---|---|---|
| 5,294,620 | A | 3/1994 | Ratcliffe et al. |
| 5,821,241 | A | 10/1998 | Claremon et al. |
| 6,841,558 | B2 | 1/2005 | Anthony et al. |
| 2003/0055071 | A1 | 3/2003 | Anthony et al. |
| 2004/0034221 | A1 | 2/2004 | Anthony et al. |
| 2005/0010048 | A1 | 1/2005 | Zhuang et al. |
| 2005/0025774 | A1 | 2/2005 | Crescenzi et al. |
| 2006/0024330 | A1 | 2/2006 | Wai et al. |

FOREIGN PATENT DOCUMENTS

| | | |
|---|---|---|
| WO | WO 00/00478 | 1/2000 |
| WO | WO 02/30426 A1 | 4/2002 |
| WO | WO 02/30930 A2 | 4/2002 |
| WO | WO 02/36734 A2 | 5/2002 |
| WO | WO 02/055079 A2 | 7/2002 |
| WO | WO 03/035076 A1 | 5/2003 |
| WO | WO 03/035077 A1 | 5/2003 |

OTHER PUBLICATIONS

Miles, PubMed Abstract (Community Pract, vol. 78, Issue 8, pp. 292-294) Aug. 2005.* van Heeswijk et al., PubMed Abstract (Antivir Ther. 6(4):201-29) Dec. 2001.*
Marcus et al., PubMed Abstract (Intervirology 45(4-6):260-6) 2002.*
Ratner, L., et al., "Complete Nucleotide Sequence of the AIDS Virus, HTLV-III", Nature, vol. 313, pp. 277-284, (1985).
Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).
Power, M.D., et al., "Nucleotide Sequence of SRV-1, a Type D Simian Acquired Immune Deficiency Syndrome Retrovirus", Science, vol. 231, pp. 1567-1572, (1986).
Pearl, L.H., et al., "A Structural Model for the Retroviral Proteases", Nature, vol. 329, pp. 351-354, (1987).
Chemical Abstract No. 33-2525, Abstract of Otiai, et al., "Synthesis of 2,5 napthyridine derivatives. II", J. Pharm. Soc. Japan, vol. 58, pp. 764-770 (1938).
Hammer, S. "Advances in antiretroviral therapy and viral load monitoring", AIDS, 1996, vol. 10, (suppl 3), pp. S1-S11.
Moyle, G. et al. "Antiretroviral Therapy for HIV Infection", Drugs, 1998, vol. 55, pp. 383-404.
Mylonakis, E. et al. "Plasma Viral Load Testing in the Management of HIV Infection A Knowledge-Based Approach to Drug Selection and Use", American Family Physician, 2001, vol. 63, pp. 483-490.
Schooley, R. "Correlation between viral load measurements and outcome in clinical trials of antiviral drugs", AIDS, 1995, vol. 9, (suppl 2), pp. S15-S19.
Amendment filed Jan. 14, 2008 in U.S. Appl. No. 10/526,275, filed Mar. 1, 2005.

* cited by examiner

Primary Examiner—Deepak Rao
(74) Attorney, Agent, or Firm—Kenneth R. Walton; Sheldon O. Heber

(57) ABSTRACT

8-Hydroxy-1-oxo-tetrahydropyrrolopyrazine compounds are inhibitors of HIV integrase and inhibitors of HIV replication. More particularly, the compounds are of Formula (I): wherein $R^1$, $R^2$, $R^3$, $R^4$, $R^5$ and $R^6$ are defined herein. The compounds are useful in the prevention and treatment of infection by ITV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines. Methods of preventing, treating or delaying the onset of AIDS and methods of preventing or treating infection by HIV are described.

(I)

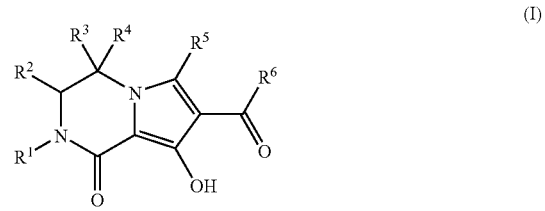

19 Claims, No Drawings

8-HYDROXY-1-OXO-TETRAHYDROPYRROLO-PYRAZINE COMPOUNDS USEFUL AS HIV INTEGRASE INHIBITORS

This application is the National Stage of International Application No. PCT/US2003/028363, filed on Sep. 10, 2003, which claims the benefit of U.S. Provisional Application No. 60/409745 (filed Sep. 11, 2002), the disclosure of which is hereby incorporated by reference in its entirety.

FIELD OF THE INVENTION

The present invention is directed to 8-hydroxy-1-oxo-tetrahydropyrrolopyrazine compounds and pharmaceutically acceptable salts thereof, their synthesis, and their use as inhibitors of the HIV integrase enzyme. The compounds of the present invention and their pharmaceutically acceptable salts are useful for preventing or treating infection by HIV and for treating, delaying the onset of, or preventing AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, integrase and an HIV protease [Toh et al., *EMBO J.* 1985, 4: 1267; Power et al., *Science* 1986, 231: 1567; Pearl et al., *Nature* 1987, 329: 351]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and of HIV replication in cells is a direct result of inhibiting the strand transfer reaction catalyzed by the recombinant integrase in vitro in HIV infected cells. A particular advantage of the present invention is highly specific inhibition of HIV integrase and HIV replication.

The following references are of interest as background:

Chemical Abstracts No. 33-2525 discloses the preparation of 5-chloro-8-hydroxy-1,6-naphthyridine-7-carboxylic acid amide from the corresponding methyl ester.

U.S. Pat. No. 5,294,620 discloses certain 1,6-naphthyridine-2-one derivatives having angiotensin II antagonist activity.

US 2003/0055071 (Publication of U.S. application Ser. No. 09/973,853, filed Oct. 10, 2001) and WO 02/30930 (Publication of International Application No. PCT/US 01/31456, filed Oct. 9, 2001) each disclose certain 8-hydroxy-1,6-naphthyridine-7-carboxamides as HIV integrase inhibitors, wherein the carboxamido nitrogen is directly or indirectly attached to phenyl or phenyl fused to a carbocycle. The carboxamides are disclosed to be useful, inter alia, for treating HIV infection and AIDS-WO 02/30426 discloses another group of 8-hydroxy-1,6-naphthyridine-7-carboxamides as HIV integrase inhibitors, wherein the carboxamido nitrogen is directly or indirectly attached to a heterocycle. WO 02/055079 discloses still another group of 8-hydroxy-1,6-naphthyridine-7-carboxamides as HIV integrase inhibitors, wherein the carboxamido nitrogen is part of a heterocyclic ring system.

WO 02/036734 discloses certain aza- and polyaza-naphthalenyl ketones to be HIV integrase inhibitors. The ketones include certain 1-aryl-1-(poly)azanaphthylenyl methanones and 1-heterocyclyl-1-(poly)azanaphthylenyl methanones. Quinolinyl, naphthyridinyl, and quinoxalinyl are disclosed as suitable (poly)azanaphthylenyl groups in the ketones.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

SUMMARY OF THE INVENTION

The present invention is directed to novel 8-hydroxy-1-oxo-tetrahydropyrrolopyrazine compounds. These compounds and their pharmaceutically acceptable salts are useful in the inhibition of HIV integrase, the prevention of infection by HIV, the treatment of infection by HIV and in the prevention, treatment, and delay in the onset of AIDS, either as compounds or their pharmaceutically acceptable salts, or as pharmaceutical composition ingredients, whether or not in combination with other HIV/AIDS antivirals, anti-infectives, immunomodulators, antibiotics or vaccines. More particularly, the present invention includes a compound of Formula (I), or a pharmaceutically acceptable salt thereof:

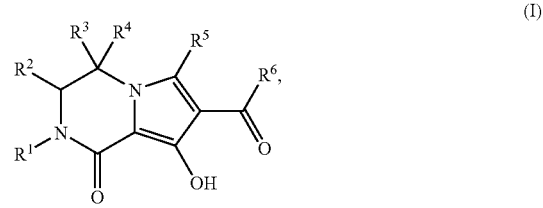

wherein $R^1$ is —H, —$C_{1-6}$ alkyl, —$C_{3-6}$ cycloalkyl, or —$C_{1-6}$ alkyl which is substituted with 1 or 2 substituents each of which is independently:

(1) $C_{3-8}$ cycloalkyl, (2) aryl, (3) a 5- or 6-membered saturated or mono-unsaturated heterocyclic ring containing from 1 to 4 heteroatoms independently selected from N, O and S, (4) a 5- or 6-membered heteroaromatic ring containing from 1 to 4 heteroatoms independently selected from N, O and S, or (5) a 9- or 10-membered fused bicyclic heterocycle containing from 1 to 4 heteroatoms independently selected from N, O and S, wherein at least one of the rings is aromatic;

wherein (A) each cycloalkyl is optionally substituted with from 1 to 3 substituents, each of which is independently halo, —$C_{1-6}$ alkyl, or —O—$C_{1-6}$ alkyl;

(B) each aryl is optionally substituted with from 1 to 5 substituents each of which is independently
  (1) —$C_{1-6}$ alkyl, optionally substituted with from 1 to 3 substituents each of which is independently —OH, —O—$C_{1-6}$ alkyl, —O—$C_{1-6}$ haloalkyl, —CN, —$NO_2$, —N($R^aR^b$), —C(=O)N($R^aR^b$), —C(=O)$R^a$, —$CO_2R^c$, —S(O)$_n R^c$, —$SO_2$N($R^aR^b$), —N($R^a$)C(=O)$R^b$, —N($R^a$)$CO_2R^c$, —N($R^a$)$SO_2R^c$, —N($R^a$)$SO_2$N($R^aR^b$), —OC(=O)N($R^aR^b$), or —N($R^a$)C(=O)N($R^aR^b$),
  (2) —O—$C_{1-6}$ alkyl, optionally substituted with from 1 to 3 substituents each of which is independently —OH, —O—$C_{1-6}$ alkyl, —O—$C_{1-6}$ haloalkyl, —S(O)$_n R^c$, —C(=O)N($R^aR^b$), —$SO_2$N($R^aR^b$), —N($R^a$)C(=O)$R^b$, —N($R^a$)$CO_2R^c$, —N($R^a$)$SO_2R^c$, —N($R^a$)$SO_2$N($R^aR^b$), —OC(=O)N($R^aR^b$), or —N($R^a$)C(=O)N($R^aR^b$),
  (3) —$C_{1-6}$ haloalkyl,
  (4) —O—$C_{1-6}$ haloalkyl,
  (5) —OH,
  (6) halo,
  (7) —CN,
  (8) —$NO_2$,
  (9) —N($R^aR^b$),
  (10) —C(=O)N($R^aR^b$),
  (11) —C(=O)$R^a$,
  (12) —$CO_2R^c$,
  (13) —$SR^c$,
  (14) —S(=O)$R^c$,
  (15) —$SO_2R^c$,
  (16) —N($R^a$)$SO_2R^c$,
  (17) —$SO_2$N($R^aR^b$),
  (18) —N($R^a$)C(=O)$R^b$, or
  (19) —N($R^a$)$CO_2R^c$;

(C) each saturated or mono-unsaturated heterocyclic ring is
  (i) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
  (ii) optionally substituted with 1 or 2 substituents each of which is independently aryl or a 5- or 6-membered heteroaromatic ring containing from 1 to 4 heteroatoms independently selected from N, O and S; and (D) each heteroaromatic ring or each fused bicyclic heterocycle is
  (i) optionally substituted with from 1 to 7 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
  (ii) optionally substituted with 1 or 2 substituents each of which is independently aryl or —$C_{1-6}$ alkyl;

$R^2$ is —H or —$C_{1-6}$ alkyl;

$R^3$ is —H, —$C_{1-6}$ alkyl, —$C_{1-6}$ haloalkyl, or —$C_{1-6}$ alkyl substituted with one of —OH, —O—$C_{1-6}$ alkyl, —O—$C_{1-6}$ haloalkyl, —CN, —$NO_2$, —N($R^aR^b$), —C(=O)N($R^aR^b$), —C(=O)$R^a$, —$CO_2R^c$, —S(O)$_n R^c$, —$SO_2$N($R^aR^b$), —N($R^a$)C(=O)$R^b$, —N($R^a$)$CO_2R^c$, —N($R^a$)$SO_2R^c$, —N($R^a$)$SO_2$N($R^aR^b$), —OC(=O)N($R^aR^b$), or —N($R^a$)C(=O)N($R^aR^b$);

$R^4$ is:
  (1) —H,
  (2) —$C_{1-6}$ alkyl optionally substituted with one of —OH, —O—$C_{1-6}$ alkyl, —O—$C_{1-6}$ haloalkyl, —CN, —$NO_2$, —N($R^aR^b$), —C(=O)N($R^aR^b$), —C(=O)$R^a$, —$CO_2R^c$, —S(O)$_n R^c$, —$SO_2$N($R^aR^b$), —N($R^a$)—C($R^b$)=O, —N($R^a$)$SO_2R^c$, —N($R^a$)$SO_2$N($R^aR^b$), —OC(=O)N($R^aR^b$), —N($R^a$)C(=O)N($R^aR^b$), —O—$C_{1-6}$ alkyl-C(=O)N($R^aR^b$), —S—$C_{1-6}$ alkyl-C(=O)N($R^aR^b$), —N($R^a$)—$C_{1-6}$ alkyl-C(=O)N($R^aR^b$), or —N($SO_2R^c$)—$C_{1-6}$ alkyl-C(=O)N($R^aR^b$),
  (3) —$C_{1-6}$ haloalkyl,
  (4) —C(=O)$R^a$,
  (5) —$CO_2R^c$,
  (6) —C(=O)N($R^aR^b$),
  (7) —$SO_2$N($R^aR^b$),
  (8) —$C_{2-6}$ alkenyl,
  (9) —$C_{2-6}$ alkenyl-C(=O)—N($R^a$)$_2$,
  (10) —$C_{2-5}$ alkynyl,
  (11) —$C_{2-5}$ alkynyl-$CH_2$N($R^a$)$_2$,
  (12) —$C_{2-5}$ alkynyl-$CH_2$O$R^a$,
  (13) —$C_{2-5}$ alkynyl-$CH_2$S(O)$_n R^c$, or
  (14) —$R^k$,
  (15) —$C_{1-6}$ alkyl substituted with $R^k$,
  (16) —$C_{1-6}$ haloalkyl substituted with $R^k$,
  (17) —$C_{1-6}$ alkyl-O—$R^k$,
  (18) —$C_{1-6}$ alkyl-O—$C_{1-6}$ alkyl-$R^k$,
  (19) —$C_{1-6}$ alkyl-S(O)$_n$—$R^k$,
  (20) —$C_{1-6}$ alkyl-S(O)$_n$—$C_{1-6}$ alkyl-$R^k$,
  (21) —$C_{1-6}$ alkyl-N($R^a$)—$R^k$,
  (22) —$C_{1-6}$ alkyl-N($R^a$)—$C_{1-6}$ alkyl-$R^k$,
  (23) —$C_{1-6}$ alkyl-N($R^a$)—$C_{1-6}$ alkyl-O$R^k$, with the proviso that the —N($R^a$)— moiety and the —O$R^k$ moiety are not both attached to the same carbon of the —$C_{1-6}$ alkyl-moiety,
  (24) —$C_{1-6}$ alkyl-C(=O)—$R^k$,
  (25) —$C_{1-6}$ alkyl-C(=O)N($R^a$)—$R^k$,
  (26) —$C_{1-6}$ alkyl-N($R^a$)C(=O)—$R^k$,
  (27) —$C_{1-6}$ alkyl-C(=O)N($R^a$)—$C_{1-6}$ alkyl-$R^k$, or
  (28) —$C_{1-6}$ alkyl-N($R^a$)—$C_{0-6}$ alkyl-S(O)$_n R^k$;

wherein $R^k$ is
  (i) aryl, which is optionally substituted with from 1 to 5 substituents each of which is independently —$C_{1-6}$ alkyl, —$C_{1-6}$ alkyl-OH, —$C_{1-6}$ alkyl-O—$C_{1-6}$ alkyl, —$C_{1-6}$ alkyl-O—$C_{1-6}$ haloalkyl, —$C_{1-6}$ alkyl-N($R^aR^b$), —$C_{1-6}$ alkyl-C(=O)N($R^aR^b$), —$C_{1-6}$ alkyl-C(=O)$R^a$, —$C_{1-6}$ alkyl-$CO_2R^c$, —$C_{1-6}$ alkyl-S(O)$_n R^c$, —O—$C_{1-6}$ alkyl, —$C_{1-6}$ haloalkyl, —O—$C_{1-6}$ haloalkyl, —OH, halo, —N($R^aR^b$), —C(=O)N($R^aR^b$), —C(=O)$R^a$, —$CO_2R^c$, —S(O)$_n R^c$, or —$SO_2$N($R^aR^b$);
  (ii) a 4 to 7-membered saturated or mono-unsaturated heterocyclic ring containing at least one carbon atom and from 1 to 4 heteroatoms independently selected from N, O and S, wherein the heterocyclic ring is:
    (a) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
    (b) optionally mono-substituted with aryl or HetA;
    wherein HetA is a 5- or 6-membered heteroaromatic ring containing from 1 to 4 heteroatoms independently selected from N, O and S, wherein the heteroaromatic ring is optionally fused with a benzene ring, and HetA is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo; or (iii) a 5- or 6-membered heteroaromatic ring containing from 1 to 4 heteroatoms independently selected from N, O and S, wherein the heteroaromatic ring is optionally substituted with from optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

$R^5$ is —H or —$C_{1-6}$ alkyl;

$R^6$ is:
(1) —OH,
(2) —O—$C_{1-6}$ alkyl,
(3) —N($R^u R^v$),
(4) —O—$C_{1-6}$ haloalkyl,
(5) —O—$C_{1-6}$ alkyl-aryl
(6) —O—$C_{1-6}$ alkyl-HetB, or
(7) —O—$C_{1-6}$ alkyl-HetC,
wherein
$R^u$ is —H or —$C_{1-6}$ alkyl;
$R^v$ independently has the same definition as $R^1$;
HetB is a 5- or 6-membered saturated or mono-unsaturated ring containing from 1 to 4 heteroatoms independently selected from N, O and S, wherein the ring is optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
HetC is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

each $R^a$ and $R^b$ is independently —H or —$C_{1-6}$ alkyl;
each $R^c$ is independently a —$C_{1-6}$ alkyl, and
each n is independently an integer equal to 0, 1 or 2.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the 8-hydroxy-1-oxo-tetrahydropyrrolopyrazines of Formula (I) above. These compounds and pharmaceutically acceptable salts thereof are HIV integrase inhibitors.

A first embodiment of the present invention is a compound of Formula (I), or a pharmaceutically acceptable salt thereof, wherein $R^1$ is —$C_{1-4}$ alkyl mono-substituted with aryl; wherein the aryl is optionally substituted with from 1 to 4 substituents each of which is independently (1) —$C_{1-4}$ alkyl, optionally mono-substituted with —OH, —O—$C_{1-4}$ alkyl, —O—$C_{1-4}$ haloalkyl, —CN, —N($R^a R^b$), —C(=O)N($R^a R^b$), —C(=O)$R^a$, —$CO_2 R^c$, —S(O)$_n R^c$, —$SO_2$N($R^a R^b$), —N($R^a$)C(=O)$R^b$, —N($R^a$)$CO_2 R^c$, —N($R^a$)$SO_2 R^c$, —N($R^a$)$SO_2$N($R^a R^b$), —OC(=O)N($R^a R^b$), or —N($R^a$)C(=O)N($R^a R^b$), (2) —O—$C_{1-4}$ alkyl, optionally mono-substituted with —OH, —O—$C_{1-4}$ alkyl, —O—$C_{1-4}$ haloalkyl, —S(O)$_n$ $R^c$, —N($R^a$)—$CO_2 R^c$, —C(=O)N($R^a R^b$), —$SO_2$N($R^a R^b$), —N($R^a$)C(=O)$R^b$, —N($R^a$)$CO_2 R^c$, —N($R^a$)$SO_2 R^c$, —N($R^a$)$SO_2$N($R^a R^b$), —OC(=O)N($R^a R^b$), or —N($R^a$)C(=O)N($R^a R^b$), (3) —$C_{1-4}$ haloalkyl,
(4) —O—$C_{1-4}$ haloalkyl,
(5) —OH,
(6) halo,
(7) —CN,
(8) —$NO_2$,
(9) —N($R^a R^b$),
(10) —$SR^c$,
(11) —S(=O)$R^c$,
(12) —$SO_2 R^c$,
(13) —N($R^a$)$SO_2 R^c$,
(14) —$SO_2$N($R^a R^b$),
(15) —N($R^a$)C(=O)$R^b$, or
(16) —N($R^a$)$CO_2 R^c$;

and all other variables are as on originally defined above.

An aspect of the first embodiment is a compound of Formula (I), or a pharmaceutically acceptable salt thereof, wherein
$R^1$ is as defined in the first embodiment;
$R^6$ is:
(1) —OH,
(2) —O—$C_{1-6}$ alkyl,
(3) —N($R^u R^v$),
(4) —O—$C_{1-6}$ haloalkyl,
(5) —O—$C_{1-6}$ alkyl-aryl
(6) —O—$C_{1-6}$ alkyl-HetB, or
(7) —O—$C_{1-6}$ alkyl-HetC,
wherein
$R^u$ is —H or —$C_{1-6}$ alkyl;
$R^v$ is —H, —$C_{1-6}$ alkyl, —$C_{3-6}$ cycloalkyl, or independently has the same definition as $R^1$ above;
HetB is a 5- or 6-membered saturated or mono-unsaturated ring containing from 1 to 4 heteroatoms independently selected from N, O and S, wherein the ring is optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
HetC is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;
and all other variables are as originally defined.

In the foregoing aspect, the reference to $R^v$ having "the same definition as $R^1$ above" means that $R^1$ in the definition of $R^v$ is as defined in the instant embodiment, here the first embodiment, instead of as originally defined.

A second embodiment of the present invention is a compound of Formula (I), or a pharmaceutically acceptable salt thereof, wherein $R^1$ is —$(CH_2)_{1-4}$-phenyl, wherein the phenyl is optionally substituted with from 1 to 3 substituents each of which is independently (1) —$C_{1-4}$ alkyl, optionally mono-substituted with —OH, —O—$C_{1-4}$ alkyl, —O—$C_{1-4}$ haloalkyl, —CN, —N(R$^a$R$^b$), —C(=O)N(R$^a$R$^b$), —C(=O)R$^a$, —CO$_2$R$^c$, S(O)$_n$R$^c$, or —SO$_2$N(R$^a$R$^b$),
(2) —O—C$_{1-4}$ alkyl,
(3) —C$_{1-4}$ haloalkyl,
(4) —O—C$_{1-4}$ haloalkyl,
(5) —OH,
(6) halo,
(7) —CN,
(8) —NO$_2$,
(9) —N(R$^a$R$^b$),
(10) —SR$^c$,
(11) —S(=O)R$^c$,
(12) —SO$_2$R$^c$,
(13) —N(R$^a$)SO$_2$R$^c$,
(14) —SO$_2$N(R$^a$R$^b$),
(15) —N(R$^a$)C(=O)R$^b$, or
(16) —N(R$^a$)CO$_2$R$^c$;

and all other variables are as originally defined above.

An aspect of the second embodiment is a compound of Formula (I), or a pharmaceutically acceptable salt thereof, wherein R$^1$ is as defined in the second embodiment, R$^6$ is as defined in the foregoing aspect of the first embodiment except that R$_1$ in the definition of R$^v$ is as defined in the second embodiment; and all other variables are as originally defined.

A third embodiment of the present invention is a compound of Formula (I), or a pharmaceutically acceptable salt thereof, wherein R$^1$ is

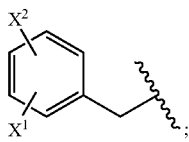

wherein X$^1$ and X$^2$ are each independently
(1) —H,
(2) methyl,
(3) ethyl,
(4) methoxy,
(5) ethoxy,
(6) —CF$_3$,
(7) fluoro,
(8) bromo, or
(9) chloro;

and all other variables are as originally defined above.

In an aspect of the third embodiment, R$^1$ is 4-fluorobenzyl. Another aspect of the third embodiment is a compound of Formula (I), or a pharmaceutically acceptable salt thereof, wherein R$^1$ is as defined in the third embodiment, R$^6$ is as defined in the foregoing aspect of the first embodiment except that R$^1$ in the definition of R$^v$ is as defined in the third embodiment; and all other variables are as originally defines In a feature of this aspect, R$^1$ is 4-fluorobenzyl.

A fourth embodiment of the present invention Is a compound of Formula (I), or a pharmaceutically acceptable salt hereof, wherein R$^2$ is is —H or —C$_{1-4}$ alkyl; and all other variables are as originally defined or as defined in any of the preceding embodiments or aspects. In an aspect of this embodiment, R$^2$ is —H.

A fifth embodiment of the present invention is a compound of Formula (I), or a pharmaceutically acceptable salt thereof, wherein R$^3$ is —H or —C$_{1-4}$ alkyl; and all other variables are as originally defined or as defined in any of the preceding embodiments or aspects thereof. In an aspect of this embodiment, R$^3$ is —H.

A sixth embodiment of the present invention is a compound of Formula (I), or a pharmaceutically acceptable salt thereof, wherein R$^4$ is:
(1) —H,
(2) —C$_{1-4}$ alkyl optionally substituted with one of —OH, —O—C$_{1-4}$ alkyl, —O—C$_{1-4}$ haloalkyl, —CN, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)—C(R$^b$)=O, —N(R$^a$)SO$_2$R$^b$, or —N(R$^a$)SO$_2$N(R$^a$R$^b$),
(3) —C(=O)N(R$^a$R$^b$),
(4) —R$^k$,
(5) —C$_{1-4}$ alkyl substituted with R$^k$,
(6) —C$_{1-4}$ alkyl-O—R$^k$, or
(7) —C$_{1-4}$ alkyl-O—C$_{1-4}$ alkyl-R$^k$;

and all other variables am as originally defined or as defined in any of the preceding embodiments or aspects thereof.

A seventh embodiment of the present invention is a compound of Formula (I), or a pharmaceutically acceptable salt thereof, wherein R$^4$ is:
(1) —H,
(2) —C$_{1-4}$ alkyl optionally substituted with one of —OH, —N(R$^a$R$^b$), or —C(=O)N(R$^a$R$^b$),
(3) —C(=O)N(R$^a$R$^b$),
(4) —(CH$_2$)$_{1-3}$—R$^k$,
(5) —(CH$_2$)$_{1-3}$—O—R$^k$, or
(6) —CH$_2$)$_{1-3}$—O—(CH$_2$)$_{1-3}$—R$^k$;

and all other variables are as originally defined or as defined in any of the first five embodiments or aspects thereof.

An eighth embodiment of the present invention is a compound of Formula (I), or a pharmaceutically acceptable salt thereof, wherein R$^k$ is:
(i) phenyl, which is optionally substituted with from 1 to 3 substituents each of which is independently —C$_{1-4}$ alkyl, —C$_{1-4}$ alkyl-OH, —C$_{1-4}$ alkyl-O—C$_{1-4}$ alkyl, —C$_{1-4}$ alkyl-O—C$_{1-4}$ haloalkyl, —C$_{1-4}$ alkyl-N(R$^a$R$^b$), —C$_{1-4}$ alkyl-C(=O)N(R$^a$R$^b$), —C$_{1-4}$ alkyl-C(=O)R$^a$, —C$_{1-4}$ alkyl-CO$_2$R$^c$, —C$_{1-4}$ alkyl-S(O)$_n$R$^c$, —O—C$_{1-4}$ alkyl, —C$_{1-4}$ haloalkyl, —O—C$_{1-4}$ haloalkyl, —OH, halo, —N(R$^a$R$^b$), —C(=O)N(R$^a$R$^b$), —C(=O)R$^a$, —CO$_2$R$^c$, —S(O)$_n$R$^c$, or —SO$_2$N(R$^a$R$^b$);
(ii) a 4 to 7-membered saturated heterocyclic ring containing at least one carbon atom and a total of from 1 to 4 heteroatoms independently selected from 1 to 4 N atoms, from 0 to 2 O atoms, and from 0 to 2 S atoms, wherein the heterocyclic ring is:
(a) optionally substituted with from 1 to 4 substituents each of which is independently halogen, —C$_{1-4}$ alkyl, —C$_{1-4}$ haloalkyl, —O—C$_{1-4}$ alkyl, O—C$_{1-4}$ haloalkyl, or oxo; and
(b) optionally mono-substituted with phenyl or HetA;
wherein HetA is a 5- or 6-membered heteroaromatic ring containing a total of from 1 to 4 heteroatoms independently selected from 1 to 4 N atoms, from 0 to 2 O atoms, and from 0 to 2 S atoms, wherein HetA is optionally substituted with from 1 to 3 substituents each of which is independently —C$_{1-4}$ alkyl, —C$_{1-4}$ haloalkyl, —O—C$_{1-4}$ alkyl, —O—C$_{1-4}$ haloalkyl, or oxo; or
(iii) a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from optionally substituted with from 1 to 3 substituents each of which is independently —$C_{1-6}$ alkyl, —$C_{1-6}$ haloalkyl, —O—$C_{1-6}$ alkyl, O—$C_{1-6}$ haloalkyl, or oxo;

and all other variables are as originally defined or as defined in any of the preceding embodiments or aspects thereof.

In an aspect of the eighth embodiment, HetA is a 5- or 6-membered heteroaromatic ring containing 1 or 2 N atoms, wherein HetA is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo. In another aspect of the eighth embodiment, HetA is pyrrolyl, pyrazolyl, imidazolyl, pyridyl, or pyrazinyl; which is optionally substituted with from 1 to 3 substituents each of which is independently —$C_{1-4}$ alkyl (e.g., methyl), —$C_{1-4}$ haloalkyl (e.g., trifluoromethyl), —O—$C_{1-4}$ alkyl (e.g., methoxy), —O—$C_{1-4}$ haloalkyl (e.g., —$OCF_3$), or oxo.

A ninth embodiment of the present invention is a compound of Formula (I), or a pharmaceutically acceptable salt thereof, wherein $R^k$ is:
(i) phenyl, which is optionally substituted with from 1 to 3 substituents each of which is independently —$C_{1-4}$ alkyl, —$C_{1-4}$ alkyl-OH, —$C_{1-4}$ alkyl-O—$C_{1-4}$ alkyl, —$C_{1-4}$ alkyl-O—$C_{1-4}$ haloalkyl, —$C_{1-4}$ alkyl-N($R^aR^b$), —$C_{1-4}$ alkyl-C(=O)N($R^aR^b$), —$C_{1-4}$ alkyl-C(=O)$R^a$, —$C_{1-4}$ alkyl-$CO_2R^c$, —$C_{1-4}$ alkyl-S(O)$_nR^c$, —O—$C_{1-4}$ alkyl, —$C_{1-4}$ haloalkyl, —O—$C_{1-4}$ haloalkyl, —OH, halo, —N($R^aR^b$), —C(=O)N($R^aR^b$), —C(=O)$R^a$, —$CO_2R^c$, —S(O)$_nR^c$, or —$SO_2$N($R^aR^b$); or
(ii) a saturated heterocyclic ring selected from the group consisting of piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, and dioxanyl; wherein the saturated heterocyclic ring is:
  (a) optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo; and
  (b) optionally mono-substituted with phenyl or HetA; wherein HetA is a heteroaromatic ring selected from the group consisting of pyridyl, pyrrolyl, pyrazinyl, pyridinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl; wherein the heteroaromatic ring is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo;

and all other variables are as originally defined or as defined in any of the first seven embodiments or aspects thereof.

A tenth embodiment of the present invention is a compound of Formula (I), or a pharmaceutically acceptable salt thereof, wherein $R^5$ is —H; and all other variables are as originally defined or as defined in any of the preceding embodiments or aspects thereof.

An eleventh embodiment of the present invention is a compound of Formula (I), or a pharmaceutically acceptable salt thereof, wherein $R^6$ is:
(1) —OH,
(2) —O—$C_{1-4}$ alkyl,
(3) —N($R^uR^v$),
(4) —O—$C_{1-4}$ haloalkyl,
(5) —O—$C_{1-4}$ alkyl-aryl
(6) —O—$C_{1-4}$ alkyl-HetB, or
(7) —O—$C_{1-4}$ alkyl-HetC,
wherein
  $R^u$ is —H or —$C_{1-4}$ alkyl;
  $R^v$ is —H, —$C_{1-4}$ alkyl, or cyclopropyl;
  HetB is a 5- or 6-membered saturated ring containing a total of from 1 to 4 heteroatoms independently selected from 1 to 4 N atoms, from 0 to 2 O atoms, and from 0 to 2 S atoms, wherein the saturated zing is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo; and
  HetC is a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo;

and all other variables are as originally defined or as defined in any of the first ten embodiments or aspects thereof A twelfth embodiment of the present invention is a compound of Formula (I), or a pharmaceutically acceptable salt thereof, wherein $R^6$ is:
(1) —OH,
(2) —O—$C_{1-4}$ alkyl,
(3) —N($R^uR^v$),
(4) —O—$C_{1-4}$ haloalkyl, or
(5) —O—$C_{1-4}$ alkyl-HetC,
wherein
  $R^u$ is —H or —$C_{1-4}$ alkyl;
  $R^v$ is —$C_{1-4}$ alkyl or cyclopropyl;
  HetC is a 5- or 6-membered heteroaromatic ring containing a total of from 1 to 4 heteroatoms independently selected from 1 to 4 N atoms, from 0 to 2 O atoms, and from 0 to 2 S atoms, wherein the zing is attached to the remainder of the compound via a ring carbon atom and a ring N atom is alpha to the ring carbon attached to the remainder of the compound; and wherein the heteroaromatic ring is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo;

and all other variables are as originally defined or as defined in any of the first ten embodiments or aspects thereof.

A first class of tie present invention includes compounds of Formula (II), or a pharmaceutically acceptable salt thereof:

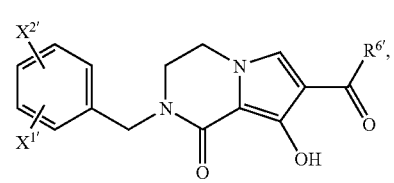

(II)

wherein:

wherein $X^{1'}$ and $X^{2'}$ are each independently:
(1) —H,
(2) $C_{1-4}$ alkyl,
(2) —O—$C_{1-4}$ alkyl, (3) —C$_{1-4}$ haloalkyl,
(4) —O—C$_{1-4}$ haloalkyl, or
(5) halo; and
R$^{6'}$ is:
(1) —OH,
(2) —O—C$_{1-4}$ alkyl, or
(3) —N(R$^u$R$^v$);
wherein
R$^u$ is —H or —C$_{1-4}$ alkyl; and
R$^v$ is —C$_{1-4}$ alkyl or cyclopropyl.

A sub-class of the first class includes compounds of Formula (II), or a pharmaceutically acceptable salt thereof, wherein:
X$^{1'}$ and X$^{2'}$ are each independently:
(1) —H,
(2) methyl,
(2) —OCH$_3$,
(3) —CF$_3$,
(4) —OCF$_3$,
(5) chloro,
(6) fluoro, or
(7) bromo; and
R$^{6'}$ is:
(1) —H,
(2) methoxy
(3) ethoxy
(4) —N(R$^u$R$^v$);
wherein
R$^u$ is —H; and
R$^v$ is methyl, ethyl, or cyclopropyl.

A second class of the present invention includes compounds of Formula (III), or a pharmaceutically acceptable salt thereof:

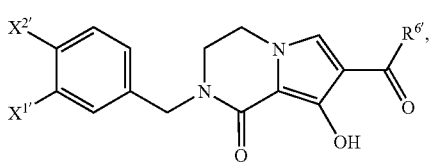

(III)

wherein X$^{1'}$ and X$^{2'}$ are each independently —H or halo; and
R$^{6'}$ is:
(1) —OH,
(2) —O—C$_{1-4}$ alkyl, or
(3) —N(R$^u$R$^v$);
wherein
R$^u$ is —H or —C$_{1-4}$ alkyl; and
R$^v$ is —C$_{1-4}$ alkyl or cyclopropyl.

A sub-class of the second class includes compounds of Formula (III), or a pharmaceutically acceptable salt thereof, wherein:
X$^{1'}$ and X$^{2'}$ are each independently —H, fluoro, chloro, or bromo; and
R$^{6'}$ is:
(1) —OH,
(2) methoxy
(3) ethoxy
(4) —N(R$^u$R$^v$);
wherein
R$^u$ is —H; and
R$^v$ is methyl, ethyl, or cyclopropyl.

A thirteenth embodiment of the present invention is a compound of Formula (IV), or a pharmaceutically acceptable salt thereof:

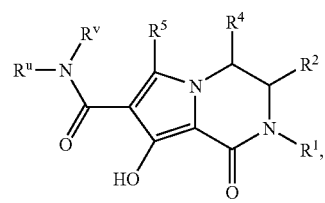

(IV)

wherein
R$^u$ is —H or —C$_{1-6}$ alkyl;
R$^v$ is C$_{1-6}$ alkyl which is substituted wit 1 or 2 substituents each of which is independently:
(1) C$_{3-8}$ cycloalkyl,
(2) aryl,
(3) a 5- or 6-membered saturated or mono-unsaturated heterocyclic ring containing from 1 to 4 heteroatoms independently selected from N, O and S,
(4) a 5- or 6-membered heteroaromatic ring containing from 1 to 4 heteroatoms independently selected from N, O and S, or
(5) a 9- or 10-membered fused bicyclic heterocycle containing from 1 to 4 heteroatoms independently selected from N, O and S, wherein at least one of the rings is aromatic;
wherein
(A) each cycloalkyl is optionally substituted with from 1 to 3 substituents, each of which is independently halo, —C$_{1-6}$ alkyl, or —O—C$_{1-6}$ alkyl;
(B) each aryl is optionally substituted with from 1 to 5 substituents each of which is independently
(1) —C$_{1-6}$ alkyl, optionally substituted with from 1 to 3 substituents each of which is independently —OH, —O—C$_{1-6}$ alkyl, —O—C$_{1-6}$ haloalkyl, —CN, —NO$_2$, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
(2) —O—C$_{1-6}$ alkyl, optionally substituted with from 1 to 3 substituents each of which is independently —OH, —O—C$_{1-6}$ alkyl, —O—C$_{1-6}$ haloalkyl, —S(O)$_n$R$^c$, —C(=O)N(R$^a$R$^b$), —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
(3) —C$_{1-6}$ haloalkyl,
(4) —O—C$_{1-6}$ haloalkyl,
(5) —OH,
(6) halo,
(7) —CN,
(8) —NO$_2$,
(9) —N(R$^a$R$^b$),
(10) —C(=O)N(R$^a$R$^b$),
(11) —C(=O)R$^a$,
(12) —CO$_2$R$^c$,
(13) —SR$^c$,
(14) —S(=O)R$^c$,
(15) —SO$_2$R$^c$,
(16) —N(R$^a$)SO$_2$R$^c$,
(17) —SO$_2$N(R$^a$R$^b$),

(18) —N(R$^a$)C(=O)R$^b$, or
(19) —N(R$^a$)CO$_2$R$^c$;
(C) each saturated or mono-unsaturated heterocyclic ring is
  (i) optionally substituted with from 1 to 5 substituents each of which is independently halogen, —C$_{1-6}$ alkyl, —C$_{1-6}$ haloalkyl, O—C$_{1-6}$ alkyl, —O—C$_{1-6}$ haloalkyl, or oxo; and
  (ii) optionally substituted with 1 or 2 substituents each of which is independently aryl or a 5- or 6-membered heteroaromatic ring containing from 1 to 4 heteroatoms independently selected from N, O and S; and
(D) each heteroaromatic ring or each fused bicyclic heterocycle is
  (i) optionally substituted with from 1 to 7 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; and
  (ii) optionally substituted with 1 or 2 substituents each of which is independently aryl or —C$_{1-6}$ alkyl-aryl;
R$^1$ is —H or —C$_{1-6}$ alkyl;

and all other variables are as originally defined above or as defined in any of the previous embodiments or aspects thereof.

A fourteenth embodiment of the present invention is a compound of Formula (IV), or a pharmaceutically acceptable salt thereof, wherein R$^v$ is —C$_{1-4}$ alkyl mono-substituted with aryl; wherein the aryl is optionally substituted with from 1 to 4 substituents each of which is independently
  (1) —C$_{1-4}$ alkyl, optionally mono-substituted with —OH, —O—C$_{1-4}$ alkyl, —O—C$_{1-4}$ haloalkyl, —CN, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
  (2) —O—C$_{1-4}$ alkyl, optionally mono-substituted with —OH, —O—C$_{1-4}$ alkyl, —O—C$_{1-4}$ haloalkyl, —S(O)$_n$R$^c$, —N(R$^a$)—CO$_2$R$^c$, —C(=O)N(R$^a$R$^b$), —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
  (3) —C$_{1-4}$ haloalkyl,
  (4) —O—C$_{1-4}$ haloalkyl,
  (5) —OH,
  (6) halo,
  (7) —CN,
  (8) —NO$_2$,
  (9) —N(R$^a$R$^b$),
  (10) —SR$^c$,
  (11) —S(=O)R$^c$,
  (12) —SO$_2$R$^c$,
  (13) —N(R$^a$)SO$_2$R$^c$,
  (14) —SO$_2$N(R$^a$R$^b$),
  (15) —N(R$^a$)C(=O)R$^b$, or
  (16) —N(R$^a$)CO$_2$R$^c$;

and all other variables are as first defined above for Formula (IV).

A fifteenth embodiment of the present invention is a compound of Formula (IV), or a pharmaceutically acceptable salt thereof, wherein R$^v$ is —(CH$_2$)$_{1-4}$-phenyl, wherein the phenyl is optionally substituted with from 1 to 3 substituents each of which is independently
  (1) —C$_{1-4}$ alkyl, optionally mono-substituted with —OH, —O—C$_{1-4}$ alkyl, —O—C$_{1-4}$ haloalkyl, —CN, —N(R$^a$R$^b$), —C(=O)N(R$^a$R$^b$), —C(=O)R$^a$, —CO$_2$R$^c$, —S(O)$_n$R$^c$, or —SO$_2$N(R$^a$R$^b$),
  (2) —O—C$_{1-4}$ alkyl,
  (3) —C$_{1-4}$ haloalkyl,
  (4) —O—C$_{1-4}$ haloalkyl,
  (5) —OH,
  (6) halo,
  (7) —CN,
  (8) —NO$_2$,
  (9) —N(R$^a$R$^b$),
  (10) —SR$^c$,
  (11) —S(=O)R$^c$,
  (12) —SO$_2$R$^c$,
  (13) —N(R$^a$)SO$_2$R$^c$,
  (14) —SO$_2$N(R$^a$R$^b$),
  (15) —N(R$^a$)C(=O)R$^b$, or
  (16) —N(R$^a$)CO$_2$R$^c$;

and all other variables are -as first defined above in Formula (IV).

A sixteenth embodiment of the present invention is a compound of Formula (IV), or a pharmaceutically acceptable salt thereof, wherein R$^v$ is:

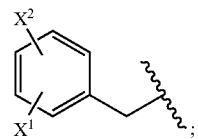

X$^1$ and X$^2$ are each independently
  (1) —H,
  (2) methyl,
  (3) ethyl,
  (4) methoxy,
  (5) ethoxy,
  (6) —CF$_3$,
  (7) fluoro,
  (8) bromo, or
  (9) chloro;

and all other variables are as first defined above in Formula (IV).

In an aspect of the sixteenth embodiment, R$^v$ is 4-fluorobenzyl.

A seventeenth embodiment of the present invention is a compound of Formula (IV), or a pharmaceutically acceptable salt thereof, wherein R$^u$ is —H; and all other variables are as first defined in Formula (IV) or as defined in the preceding embodiments or aspects thereof.

An eighteenth embodiment of the present invention is a compound of Formula (IV), or a pharmaceutically acceptable salt thereof, wherein R$^5$ is —H; and all other variables are as first defined in Formula (IV) or as defined in the preceding embodiments or aspects thereof.

A nineteenth embodiment of the present invention is a compound of Formula (IV), or a pharmaceutically acceptable salt thereof, wherein R$^4$ is:
  (1) —H,
  (2) —C$_{1-4}$ alkyl optionally substituted with one of —OH, —N(R$^a$R$^b$), or —C(=O)N(R$^a$R$^b$),
  (3) —C(=O)N(R$^a$R$^b$),
  (4) —(CH$_2$)$_{1-3}$—R$^k$,
  (5) —(CH$_2$)$_{1-3}$—O—R$^k$, or
  (6) —(CH$_2$)$_{1-3}$—O—(CH$_2$)$_{1-3}$—R$^k$;

and all other variables are as first defined in Formula (IV) or as defined in the preceding embodiments or aspects thereof.

A twentieth embodiment of the present invention is a compound of Formula (IV), or a pharmaceutically acceptable salt thereof, wherein $R^k$ is the same as defined above in the eighth embodiment for compounds of Formula (I); and all other variables are as originally defined in Formula (IV) or as defined in any of the preceding embodiments or aspects thereof.

In an aspect of the twentieth embodiment, HetA is a 5- or 6-membered heteroaromatic ring containing 1 or 2 N atoms, wherein HetA is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo. In another aspect of the eighth embodiment, HetA is pyrrolyl, pyrazolyl, imidazolyl, pyridyl, or pyrazinyl; which is optionally substituted with from 1 to 3 substituents each of which is independently —$C_{1-4}$ alkyl (e.g., methyl), —$C_{1-4}$ haloalkyl (e.g., trifluoromethyl), —O—$C_{1-4}$ alkyl (e.g., methoxy), —O—$C_{1-4}$ haloalkyl (e.g., —$OCF_3$), or oxo.

A twenty first embodiment of the present invention is a compound of Formula (IV), or a pharmaceutically acceptable salt thereof, wherein $R^k$ is the same as defined above in the ninth embodiment for compounds of Formula (I); and all other variables are as originally defined in Formula (IV) or as defined in any of the preceding embodiments or aspects thereof.

A twenty-second embodiment of the present invention is a compound of Formula (IV), or a pharmaceutically acceptable salt thereof, wherein $R^2$ is —H; and all other variables are as originally defined or as defined in the preceding embodiments or aspects thereof.

A twenty third embodiment of the present invention is a compound of Formula (IV), or a pharmaceutically acceptable salt thereof, wherein $R^1$ is —$C_{1-4}$ alkyl; and all other variables are as originally defined or as defined in the preceding embodiments or aspects thereof. In an aspect of this embodiment, $R^1$ is methyl or ethyl.

A twenty fourth embodiment of the present invention is a compound of Formula (IV), or a pharmaceutically acceptable salt thereof, wherein $R^1$ is —H, methyl, or ethyl; and all other variables are as originally defined or as defined in the preceding embodiments or aspects thereof.

A twenty-fifth embodiment of the present invention is a compound selected from the group consisting of:
ethyl 2-benzyl-8-hydroxy-1-oxo-1,2,3,4-tetrahydropyrrolo[1,2-α]pyrazine-7-carboxylate;
2-benzyl-8-hydroxy-1-oxo-1,2,3,4-tetrahydropyrrolo[1,2-α]pyrazine-7-carboxylic acid;
ethyl 2-(4-fluorobenzyl)-8-hydroxy-1-oxo-1,2,3,4-tetrahydropyrrolo[1,2-α]pyrazine-7-carboxylate;
2-(4-fluorobenzyl)-8-hydroxy-1-oxo-1,2,3,4-tetrahydropyrrolo[1,2-α]pyrazine-7-carboxylic acid;
2-(4-fluorobenzyl)-8-hydroxy-N-methyl-1-oxo-1,2,3,4-tetrahydropyrrolo[1,2-α]pyrazine-7-carboxamide;
2-(4-fluorobenzyl)-8-hydroxy-N-ethyl-1-oxo-1,2,3,4-tetrahydropyrrolo[1,2-α]pyrazine-7-carboxamide;
2-(4-fluorobenzyl)-8-hydroxy-N-cycopropyl-1-oxo-1,2,3,4-tetrahydropyrrolo[1,2-α]pyrazine-7-carboxamide;
ethyl 2-(3-chlorobenzyl)-8-hydroxy-1-oxo-1,2,3,4-tetrahydropyrrolo[1,2-α]pyrazine-7-carboxylate;
2-(3-chlorobenzyl)-8-hydroxy-1-oxo-1,2,3,4-tetrahydropyrrolo[1,2-α]pyrazine-7-carboxylic acid;
N-(4-fluorobenzyl)-8-hydroxy-2-methyl-1-oxo-1,2,3,4-tetrahydropyrrolo[1,2-α]pyrazine-7-carboxamide;
ethyl 2-(3-fluorobenzyl)-8-hydroxy-1-oxo-1,2,3,4-tetrahydropyrrolo[1,2-α]pyrazine-7-carboxylate;
ethyl 2-(3,4-fluorobenzyl)-8-hydroxy-1-oxo-1,2,3,4-tetrahydropyrrolo[1,2-α]pyrazine-7-carboxylate;
ethyl 2-(4-chlorobenzyl)-8-hydroxy-1-oxo-1,2,3,4-tetrahydropyrrolo[1,2-α]pyrazine-7-carboxylate;
ethyl 2-(3-chloro-4-fluorobenzyl)-8-hydroxy-1-oxo-1,2,3,4-tetrahydropyrrolo[1,2-α]pyrazine-7-carboxylate;
ethyl 2-(3,4-dichlorobenzyl)-8-hydroxy-1-oxo-1,2,3,4-tetrahydropyrrolo[1,2-α]pyrazine-7-carboxylate;
2-(4-chlorobenzyl)-8-hydroxy-N-methyl-1-oxo-1,2,3,4-tetrahydropyrrolo[1,2-α]pyrazine-7-carboxamide;
2-(3,4-difluorobenzyl)-8-hydroxy-N-methyl-1-oxo-1,2,3,4-tetrahydropyrrolo[1,2-α]pyrazine-7-carboxamide;
2-(3,4-dichlorobenzyl)-8-hydroxy-N-methyl-1-oxo-1,2,3,4-tetrahydropyrrolo[1,2-α]pyrazine-7-carboxamide;

and pharmaceutically acceptable salts thereof.

Other embodiments of the present invention include compounds of Formula (I) and (IV) respectively, wherein each $R^a$ and $R^b$ is independently —H or —$C_{1-4}$ alkyl; each $R^c$ is independently a —$C_{1-4}$ alkyl; and all other variables are as originally defined or as defined in any of the foregoing embodiments or aspects thereof.

Still other embodiments of the present invention include compounds of Formula (I) and (IV) respectively, wherein each $R^a$ and $R^b$ is independently —H, methyl, or ethyl; each $R^c$ is independently methyl or ethyl; and all other variables are as originally defined or as defined in any of the foregoing embodiments or aspects thereof.

Other embodiments of the present invention include the following:

(a) A pharmaceutical composition comprising a therapeutically effective amount of a compound of the invention (e.g., a compound of Formula (I) or Formula (II) or Formula (III) or Formula (IV) or any of the specific compounds set forth above) and a pharmaceutically acceptable carrier.

(b) A pharmaceutical composition which comprises the product prepared by combining (e.g., mixing) a therapeutically effective amount of a compound of the invention and a pharmaceutically acceptable carrier.

(c) The pharmaceutical composition of (a) or (b), further comprising a therapeutically effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of the invention and a therapeutically effective amount of an HIV infection/AIDS treatment agent selected from the group consisting of HIV/AIDS antiviral agents, immunomodulators, and anti-infective agents.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of the invention.

(h) A method of preventing or treating infection by HIV in a subject in need thereof which comprises administering to the subject a therapeutically effective amount of a compound of the invention.

(i) The method of (h), wherein the compound of the invention is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of the invention.

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(l) A method of inhibiting M integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV protease, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, or an aspect or feature or sub-feature thereof, described above, In all of the foregoing embodiments describing compositions, combinations and methods, the compound may optionally be used in the form of a pharmaceutically acceptable salt.

As used herein, the term "$C_{1-6}$ alkyl"(or "$C_1$-$C_6$ alkyl") means a linear or branched chain alkyl group having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "$C_0$" as employed in expressions such as "—$C_{0-6}$ alkyl-" means a direct covalent bond. For example, in the group —$C_{1-6}$ alkyl-N($R^a$)—$C_{0-6}$ alkyl-S(O)$_n$$R^k$, when the second alkylene group is "$C_0$", then the group is —$C_{1-6}$ alkyl-N($R^a$)—S(O)$_n$$R^k$.

The term "—$C_{1-6}$ alkyl-" refers to a $C_1$ to $C_6$ linear or branched alkyl group as just defined which is bivalent. It can alternatively be referred to as "$C_{1-6}$ alkylene" or "$C_{1-6}$ alkanediyl". A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—.

The term "$C_{2-6}$ alkenyl"(or "$C_2$-$C_6$ alkenyl") means a linear or branched chain alkenyl group having from 2 to 6 carbon atoms and includes all of the hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-4}$ alkenyl" have an analogous meaning. A class of alkenyls of particular interest with respect to the invention is —$CH_2$=CH—$(CH_2)_{0-4}$H, and sub-classes of particular interest include —CH=CH—$(CH_2)_{1-2}$H, —CH=CH—$CH_3$, and —CH=$CH_2$. Another class of alkenyls of particular interest with respect to the invention is alkenyls selected from —$(CH_2)_2$—CH=CH—$(CH_2)_{0-2}$H and —$CH_2$—CH=CH—$(CH_2)_{0-3}$H.

The term "$C_{2-5}$ alkenyl" (or "$C_2$-$C_5$ alkenyl") means a linear or branched chain alkenyl group having from 2 to 5 carbon atoms and includes all of the pentenyl isomers as well as 1-butynyl, 2-butynyl, 3-butynyl, 1-propynyl, 2-propynyl, and ethynyl (or acetylenyl). Similar terms such as "$C_{2-4}$ alkynyl" have an analogous meaning. A class of alkynyls of particular interest with respect to the invention is —C≡C—$(CH_2)_{1-4}$H (e.g., —C≡C—$CH_3$). Another class of alkynyls of particular interest with respect to the invention is alkynyls selected from —$CH_2$≡$(CH_2)_{1-3}$H and —$(CH_2)_2$≡$(CH_2)_{1-2}$H.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). Similar teems such as "$C_{3-6}$ cycloalkyl" have an analogous meaning.

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning The term "$C_{1-6}$ fluoroalkyl" has an analogous meaning except that the halogen substituents are restricted to fluoro. A class of fluoroalkyls of particular interest with respect to the invention is the series $(CH_2)_{0-4}CF_3$ (i.e., trifluoromethyl, 2,2,2-trifluoroethyl, 3,3,3-trifluoro-n-propyl, etc.).

The term "oxo" means a divalent oxygen substituent; i.e., =O. An oxo substituent on a carbon atom in a heteroaromatic ring refers to the keto form of the keto-enol tautomer, as exemplified here for an oxopyridinyl substituent:

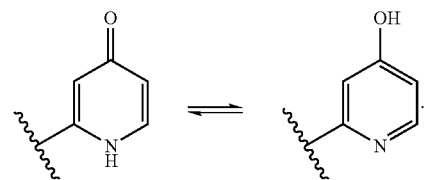

Compounds of the present invention having an oxo substituent on a carbon atom of a heteroaromatic ring are understood to include compounds in which only the keto form is present, compounds in which only the enol form is present, and compounds in which the keto and enol forms are both present.

The term "aryl" as used herein refers to an aromatic carbocyclic ring or an aromatic carbocyclic fused ring system.

The fused ring system contains two or more carbocyclic rings in which each ring shares two adjacent carbon atoms with at least one other ring. The aryl group may be attached to the rest of the molecule at any carbon atom which results in a stable compound. A subset of aryl groups particularly suitable for use in the present invention (e.g., in the definition of $R^k$) includes those selected from phenyl, naphthyl, anthryl, and phenanthryl. Another particularly suitable subset of aryl groups is phenyl and naphthyl. Still another particularly suitable subset of aryl groups is phenyl per se.

The term "heterocyclic ring" refers to a 4 to 8-membered, saturated or unsaturated monocyclic ring that contains one or more heteroatoms (e.g., from 1 to 6 heteroatoms, from 1 to 5 heteroatoms, from 1 to 4 heteroatoms, from 1 to 3 heteroatoms, 1 or 2 heteroatoms, or 1 heteroatom) independently selected from N, O and S and a balance of carbon atoms (the ring typically contains at least one carbon atom); and wherein any one or more of the nitrogen and sulfur heteroatoms is optionally oxidized, and any one or more of the nitrogen heteroatoms is optionally quaternized. The heterocyclic Ting may be attached to the rest of the molecule via any heteroatom or carbon atom in the ring, provided that attachment results in the creation of a stable structure. When the heterocyclic ring has substituents, it is understood that the substituents may be attached to any atom in the ring, whether a heteroatom or a carbon atom, provided that a stable chemical structure results.

A subset of the heterocyclic rings useful in the present invention (e.g., in the definition of $R^k$) includes any 4 to 7-membered saturated or mono-unsaturated heterocyclic ring, wherein the ring contains at least one carbon atom and from 1 to 4 heteroatoms independently selected from N, O and S. A subgroup of this subset includes any 4- to 7-membered saturated or mono-unsaturated heterocyclic ring in which the ring contains at least one carbon atom and a total of from 1 to 4 heteroatoms independently selected from 1 to 4 N atoms, from 0 to 2 O atoms, and from 0 to 2 S atoms. Representative examples of saturated heterocyclic rings include piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, tetrahydrothienyl, pyrazolidinyl, hexahydropyrimidinyl, thiazinanyl

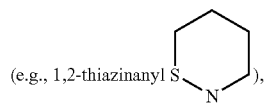

(e.g., 1,2-thiazinanyl), thiazepanyl, thiadiazepanyl, dithiazepanyl, azepanyl

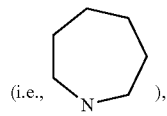

(i.e., ), diazepanyl, thiadiazinanyl

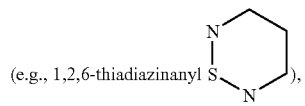

(e.g., 1,2,6-thiadiazinanyl), and dioxanyl. Representative examples of mono-unsaturated rings are the same as the saturated rings listed in the preceding sentence except that each zing contains a double bond.

Another subset of the heterocyclic rings useful in the present invention (e.g., in the definition of HetB) includes any 5- or 6-membered saturated or mono-unsaturated ring containing from 1 to 4 heteroatoms independently selected from N, O and S. A useful subgroup of this subset includes any 5- or 6-membered saturated or mono-unsaturated heterocyclic ring in which the ring contains at least one carbon atom and a total of from 1 to 4 heteroatoms independently selected from 1 to 4 N atoms, from 0 to 2 O atoms, and from 0 to 2 S atoms. Another useful subgroup is identical to the preceding subgroup, except that it is limited to saturated heterocyclic rings. Still another subgroup of this subset of heterocyclic rings suitable for use in the present invention includes any 5- or 6-membered saturated ring containing 1 or 2 N atoms and carbon atoms. Representative examples of this subgroup include piperidinyl, pyrazolidinyl, imidazolidinyl, piperazinyl, piperidinyl, and hexahydropyrimidinyl.

Still another subset of the heterocyclic rings useful in the present invention are the heteroaromatic rings. The term "heteroaromatic ring" (alternatively "heteroaryl ring") generally refers to a heterocyclic ring as defined above in which the ring is an aromatic ring A useful subgroup of this subset (e.g., in the definition of $R^k$, HetA, or HetC) includes any 5- or 6-membered monocyclic aromatic ring which consist of carbon atoms and from 1 to 4 heteroatoms independently selected from N, O and S. Representative examples of this subgroup include pyridyl, pyrrolyl, pyrazinyl, pyrimidinyl, pyridazinyl, triazinyl, thienyl (or thiophenyl), thiazolyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Another useful subgroup of this subset includes any 5- or 6-membered heteroaromatic ring in which the ring contains a total of from 1 to 4 heteroatoms independently selected from 1 to 4 N atoms, from 0 to 2 O atoms, and from 0 to 2 S atoms. Another useful subgroup includes any 5- or 6-membered heteroaromatic ring containing 1 or 2 N atoms and carbon atoms The term "fused bicyclic heterocycle" refers to any 8- to 12-membered bicyclic ring system containing one or more heteroatoms (e.g., from 1 to 6 heteroatoms, from 1 to 5 heteroatoms, from 1 to 4 heteroatoms, from 1 to 3 heteroatoms, 1 or 2 heteroatoms, or 1 heteroatom) independently selected from N, O and S, in which one ring contains all of the heteroatoms or each ring contains at least one of the heteroatoms, and wherein each ring is saturated or unsaturated, and two adjacent ring atoms are shared by each of the rings in the ring system and each of the two shared atoms is independently a carbon atom or a heteroatom. Any one or more of the nitrogen and sulfur heteroatoms in the ring system is optionally oxidized, and any one or more of the nitrogen heteroatoms is optionally quaternized. The fused bicyclic heterocycle may be attached to the rest of the molecule via any heteroatom or carbon atom in the ring, provided that attachment results in the creation of a stable structure. When the bicyclic heterocycle has substituents, it is understood that the substituents may be attached to any atom in the ring, whether a heteroatom or a carbon atom, provided that a stable chemical structure results.

A subset of the fused bicyclic heterocycles useful in the present invention (e.g., in the definition of $R^1$) includes any 9- or 10-membered fused bicyclic heterocycle containing from 1 to 4 heteroatoms independently selected from N, O and S, wherein at least one of the rings is aromatic. Representative examples of bicyclic heterocycles in this subset include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroquinolinyl, isoquinolinyl, 2,3-dihydrobenzofuranyl, 2,3-dihydrobenzo-1,4-dioxinyl (i.e., 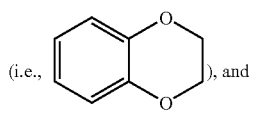), and and benzo-1,3-dioxolyl (i.e., 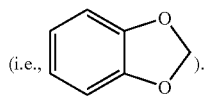).

Unless expressly stated to the contrary, an "unsaturated" ring is a partially or fully unsaturated ring.

Unless expressly stated to the contrary, all ranges cited herein are inclusive. For example, a heterocyclic Ting described as containing from "1 to 4 heteroatoms" means the ring can contain 1, 2, 3 or 4 heteroatoms.

When any variable (e.g., $R^a$, $R^b$, or $R^c$) occurs more than one time in any constituent or in Formula (I) or in any other formula depicting and describing compounds of the invention, its definition on each occurrence is independent of its definition at every other occurrence. Also, combinations of substituents and/or variables are permissible only if such combinations result in stable compounds.

The term "substituted" (e-g., as in "each aryl is optionally substituted with from 1 to 5 substituents . . .") includes mono- and poly-substitution by a named substituent to the extent such single and multiple substitution (including multiple substitution at the same site) is chemically allowed.

The symbol " ~~~ " in front of an open bond in the structural formula of a group marks the point of attachment of the group to the rest of the molecule.

The compounds of the present invention may have asymmetric centers and may occur, except when specifically noted as mixtures of stereoisomers or as individual diastereomers, or enantiomers, with all isomeric forms being included in the present invention.

As would be recognized by one of ordinary skill in the art, all of the compounds of the present invention can exist as tautomers such as the following:

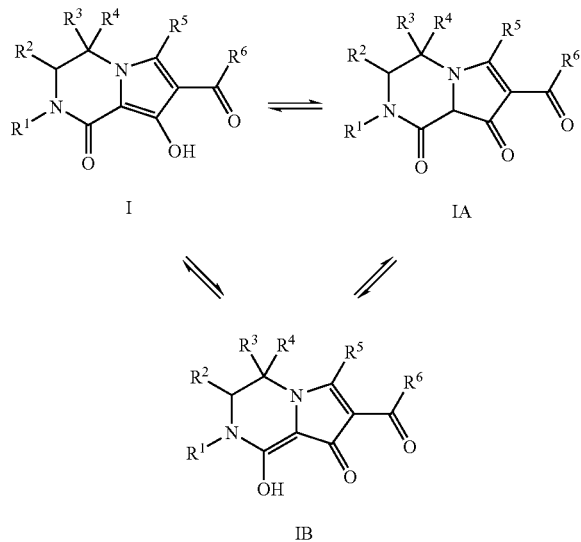

It is to be understood for the purposes of the present invention that a reference herein to a compound of Formula (I) is a reference to compound I per se, or to any one of its tautomers per se (e.g., IA or IB), or to mixtures of two or more of the tautomers (e.g., two or more of I, IA, and IB).

The compounds of the present invention are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such leans as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of preventing or treating HIV infection or preventing, treating or delaying the onset of AIDS, the compounds of the present invention can be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional non-toxic pharmaceutically-acceptable carriers, adjuvants and vehicles.

The term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HIV infection or AIDS), "administration" and its variants are each understood to include concurrent and sequential provision of the compound and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (which may be alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. When the active compound (i.e., active ingredient) is administered as the salt, references to the amount of active ingredient are to the free acid or free base form of the compound.

The pharmaceutical compositions can be in the form of orally-administrable suspensions or tablets or capsules, nasal sprays, sterile injectable preparations, for example, as sterile injectable aqueous or oleagenous suspensions or suppositories. These compositions can be prepared by methods and contain excipients which are well known in the art. Suitable methods and ingredients are described in *Remington's Pharmaceutical Sciences*, 18$^{th}$ edition, edited by A. R. Gennaro, Mack Publishing Co., 1990, which is herein incorporated by reference in its entirety.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more of the HIV/AIDS antivirals, immunomodulators, antiinfectives, or vaccines useful for treating HIV infection or AIDS. Suitable antiviral agents include those listed in the following Table:

| Drug Name | Manufacturer (Tradename and/or Location) | Indication (Activity) |
| --- | --- | --- |
| abacavir GW 1592 1592U89 | (Glaxo Welcome (ZIAGEN ®0) | HIV infection, AIDS, ARC (nRTI) |
| abacavir + lamivudine + zidovudine | GlaxoSmithKline (TRIZIVIR ®) | HIV infection, AIDS, ARC (nRTIs) |
| acemannan | Carrington Labs (Irving, TX) | ARC |
| ACH 126443 | Achillion Pharm. | Hiv infections, AIDS, ARC (nRTI) |
| acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| adefovir dipivoxil GS 840 | Gilead | HIV infection, AIDS, ARC (reverse transcriptase inhibitor) |
| AL-721 | Ethigen (Los Angeles, CA) | ARC, PGL, HIV positive, AIDS |
| alpha interferon | GlaxoSmithKline | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | GlaxoSmithKline (AGENERASE ®) | HIV infection, AIDS, ARC (PI) |
| ansamycin LM 427 | Adria Laboratories (Dublin, OH) Erbamont (Stamford, CT) | ARC |
| antibody which neutralizes pH labile alpha aberrant interferon | Advanced Biotherapy Concepts (Rockville, MD) | AIDS, ARC |

-continued

| Drug Name | Manufacturer (Tradename and/or Location) | Indication (Activity) |
|---|---|---|
| AR177 | Aronex Pharm | HIV infection, AIDS, ARC |
| atazanavir (BMS 232632) | Bristol-Myers Squibb (REYATAZ ™) | HIV infection, AIDS, ARC (PI) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (PI) |
| BMS-234475 (CGP-61755) | Bristol-Myers Squibb/ Novartis | HIV infection, AIDS, ARC (PI) |
| capravirine (AG-1549, S-1153) | Pfizer | HIV infection, AIDS, ARC (nnRTI) |
| CI-1012 | Warner-Lambert | HIV-4 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (nnRTI) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nucleosodie reverse transcriptase inhibitor) |
| ddI (didanosine, dideoxyinosine) | Bristol-Myers Squibb (VIDEX ®) | HIV infection, AIDS, ARC; combination with AZT/d4T (nRTI) |
| DPC 681 & DPC 684 | DuPont | HIV infection, AIDS, ARC (PIs) |
| DPC 961 & DPC 083 | Bristol-Myers Squibb (from DuPont Pharma) | HIV infection AIDS, ARC (nnRTIs) |
| EL10 | Elan Corp, PLC (Gainesville, GA) | HIV infection |
| efavirenz (DMP 266) | Bristol-Myers Squibb (SUSTIVA ®) Merck (STOCRIN ®) | HIV infection, AIDS, ARC (non-nucleoside RT inhibitor) |
| famciclovir | Novartis (FAMVIR ®) | herpes zoster, herpes simplex |
| emtricitabine FTC | Gilead (from Triangle Pharmaceuticals) (COVIRACIL ®) Emory University | HIV infection, AIDS, ARC (nRTI) |
| emvirine | Gilead (from Triangle Pharmaceuticals) (COACTINON ®) | HIV infection, AIDS, ARC (nnRTI) |
| enfuvirtide T-20 | Trimeris & Roche (FUZEON ®) | HIV infection, AIDS, ARC (fusion inhibitor) |
| HBY097 | Hoechst Marion Roussel | HIV infection, AIDS, ARC (nnRTI) |
| fosamprenavir | Glaxo Smith Kline | HIV infection, AIDS, ARC (prodrug of amprenavir) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, (PI) |
| ISIS 2922 | ISIS Pharmaceuticals | CMV retinitis |
| JE2147/AG1776 | Agouron | HIV infection, AIDS, ARC (PI) |
| KNI-272 | Nat'l Cancer Institute | HIV-assoc. diseases |
| lamivudine, 3TC | GlaxoSmithKline (EPIVIR ®) | HIV infection, AIDS, ARC (nRTI) |
| lamivudine + zidovudine | GlaxoSmithKline (COMBIVIR ®) | HIV infection, AIDS, ARC (nRTI) |
| lobucavir | Bristol-Myers Squibb | CMV infection |
| lopinavir (ABT-378) | Abbott | HIV infection, AIDS, ARC (PI) |
| lopinavir + ritonavir (ABT-378/r) | Abbott (KALETRA ®) | HIV infection, AIDS, ARC (PI) |
| mozenavir (DMP-450) | AVID (Camden, NJ) | HIV infection, AIDS, ARC (PI) |

-continued

| Drug Name | Manufacturer (Tradename and/or Location) | Indication (Activity) |
|---|---|---|
| nelfinavir | Agouron (VIRACEPT ®) | HIV infection, AIDS, ARC (PI) |
| nevirapine | Boeheringer Ingleheim (VIRAMUNE ®) | HIV infection, AIDS, ARC (nnRTI) |
| novapren | Novaferon Labs, Inc. (Akron, OH) | HIV inhibitor |
| peptide T octapeptide sequence | Peninsula Labs (Belmont, CA) | AIDS |
| PRO 140 | Progenics | HIV infection, AIDS, ARC (CCR5 co-receptor inhibitor) |
| PRO 542 | Progenics | HIV infection, AIDS, ARC (attachment inhibitor) |
| trisodiuin phosphonoformate | Astra Pharm. Products, Inc | CMV retinitis, HIV infection, other CMV infections |
| PNU-140690 | Pharmacia Upjohn | HIV infection, AIDS, ARC (PI) |
| probucol | Vyrex | HIV infection, AIDS |
| RBC-CD4 | Sheffield Med. Tech (Houston TX) | HIV inCection, AIDS, ARC |
| ritonavir (ABT-538) | Abbott (NORVIR ®) | HIV infection, AIDS, ARC (PI) |
| saquinavir | Hoffmann-LaRoche (FORTOVASE ®) | HIV infection, AIDS, ARC (PI) |
| stavudine; d4T didehydrodeoxy- thymidine | Bristol-Myers Squibb (ZERIT ®) | HIV infection, AIDS, ARC (nRTI) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nucleotide reverse transcriptase inhibitor) |
| tipranavir (PNU-140690) | Boebringer Ingelheim | HIV infection, AIDS, ARC (PI) |
| TMC-120 & TMC-125 | Tibotec | HIV infections, AIDS, ARC (nnRTIs) |
| TMC-126 | Tibotec | HIV infection, AIDS, ARC (PI) |
| valaciclovir | GlaxoSmithKline | genital HSV & CMV infections |
| virazole ribavirin | Viratek/ICN (Costa Mesa, CA) | asymptomatic HIV positive, LAS, ARC |
| zidovudine; AZT | GlaxoSimthKline (RETROVIR ®) | HIV infection, AIDS, ARC, Kaposi's sarcoma in combination with other therapies (nRTI) |

PI = protease inhibitor
nnRTI = non-nucleoside reverse transcriptase inhibitor
nRTI = nucleoside reverse transcriptase inhibitor A compound of the present invention can also be administered in combination with an HIV integrase inhibitor such as a compound described in WO 99/62513, WO 99/62520, or WO 99/62897. A compound of the present invention can also be administered in combination with a CCR5 receptor antagonist, such as a compound described in WO 99/04794, WO 99/09984, WO 99138514, WO 00/59497, WO 00159498, WO 00/59502, WO 00/59503, WO 00/76511, WO 00/76512, WO 00/76513, WO 00/76514, WO 00/76792, or WO 00/76793. The compounds of this invention may be effectively administered, whether at periods of pre-exposure and/or post-exposure, in combination with effective amounts of one or more HIV/AIDS antivirals, immunomodulators, anti infectives, or vaccines useful for treating HIV infection or AIDS disclosed in the Table in WO 02130930, which is herein incorporated by reference in its entirety.

It will be understood that the scope of combinations of the compounds of this invention with HIV/AIDS antivirals, immunomodulators, ant;-infectives or vaccines is not limited to those described or referenced above, but includes in principle any combination with any pharmaceutical composition useful for the treatment of AIDS. The HIV/AIDS antivirals and other agents will typically be employed in these combinations in their conventional dosage ranges and regimens as reported in the art, including the dosages described in the *Physicians' Desk Reference*, $54^{th}$ edition, Medical Economics Company, 2000. The dosage ranges for a compound of the invention in these combinations are the same as those set forth above.

Abbreviations used in the instant specification, particularly the Schemes and Examples, include the following:
AIDS=acquired immunodeficiency syndrome
ARC=AIDS related complex Bn=benzyl
DMF=dimethylformamide
DMSO=dimethyl sulfoxide
ES-MS=eletron spray mass spectroscopy
Et=ethyl
HIV=human immunodeficiency virus
HPLC=high performance liquid chromatography
LC=liquid chromatography
LiHMDS=lithium hexamethyldisilazide
Me=methyl
MS=mass spectroscopy
NaHMDS=sodium hexamethyldisilazide
NMR=nuclear magnetic resonance
TFA=trifluoroacetic acid
THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

A general method for the preparation of compounds of the present invention embraced by Formula (I) is shown in Scheme 1, wherein piperazin-2-one 1-3 is treated with dialkylalkoxymethylenemalonate 1-4 and then with a deprotonating agent (e.g., Li or Na bis(trimethylsilyl)amide or Na hydride) at low temperature (e.g., from about 0 to about 25° C.) in an anhydrous non-protic solvent (e.g., DMF or THF) to give alkyl 8-hydroxy-1-oxo-1,2,3,4-tetrahydropyrrolopyrazine-7-carboxylate 1-6. The carboxylate 1-6 can be hydrolyzed to give the 7-carboxylic acid 1-7 Carboxylate 1-6 can also be treated with amine to give the 7-carboxamide 1-8.

The piperazin-2-one 1-3 reactant can be obtained by alkylation of amine-protected piperazin-2-one 1-1 followed by deprotection to afford 1-3, as depicted in Scheme 1. Compound 1-1 can be prepared using methods described in Choi et al., *J. Med. Chem.* 1999, 3647; Najman-Bronzewska et al., *Pharmazie* 1997, 198; Fryer et al., *J. Org. Chem.* 1991, 3715, Dinsmore et al, *Organic Prep. & Procedures International.* 2002, 369, or routine variations thereof. An alternative method for preparing piperazin-2-one 1-3 is described in Bernotas et al., *Tetrahedron Lett.* 1996, 7339; Saari et al., *J. Med. Chem.* 1990, 2590; Sugihara et al., *J. Med. Chem.* 1998, 489, Dinsmore et al, *Organic Prep. & Procedures International.* 2002, 369, or routine variations thereof.

Some of the suitable dialkylalkoxymethylenemalonates 1-4 are commercially available (e.g., diethylethoxymethylenemalonate or dimethylmethoxy-methylenemalonate). Others can be obtained by preparative methods known in the art; e.g., heterocyclylalkyloxymethylene malonates can be prepared by the method described in Boger et al., *J. Org. Chem.* 1988, 3408, or routine variations thereof.

The protection and deprotection of the amine in the piperazin-2-one can be accomplished using conventional amine protecting groups, such as those described in *Protective Groups in Organic Chemistry*, ed, J. F. W. McOmie, Plenum Press, 1973 and in T. W. Greene & P. G. M. Wuts, *Protective Groups in Organic Synthesis*, John Wiley & Sons, 1991.

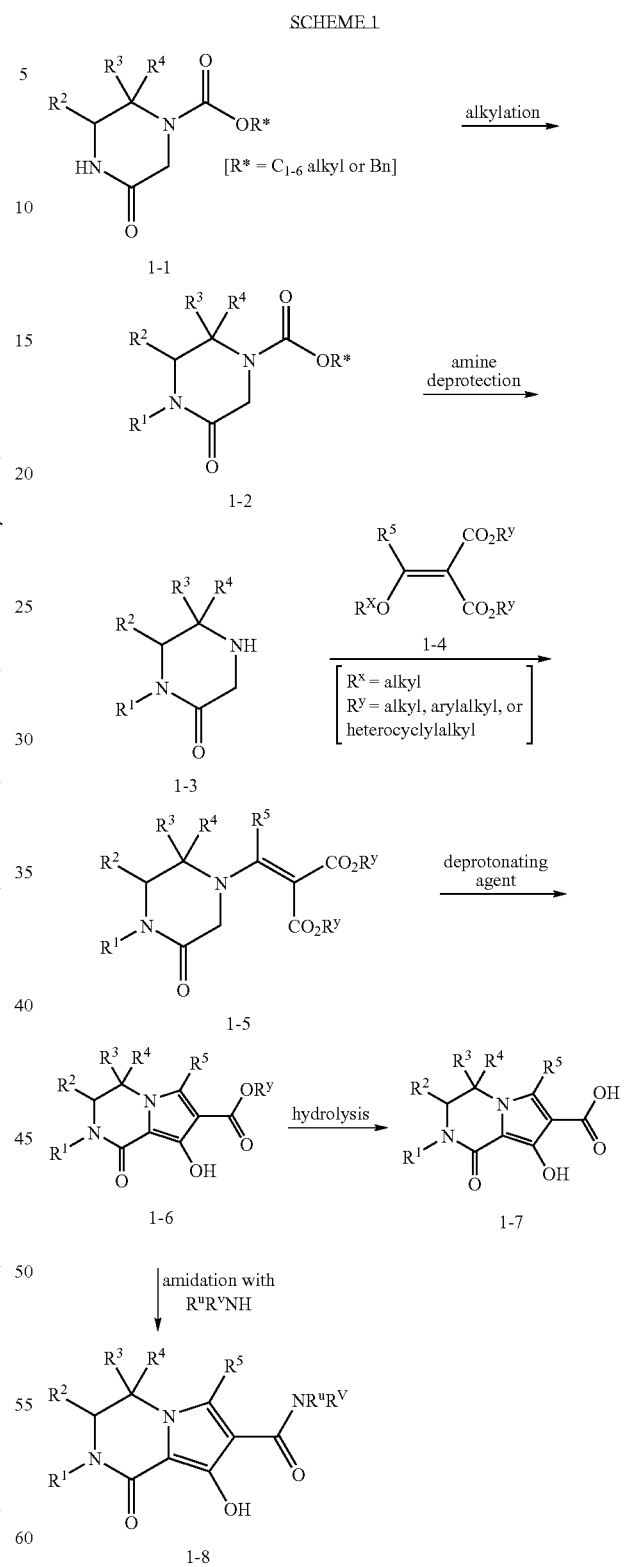

Scheme 2 exemplifies the same approach as set forth in Scheme 1 for the preparation of compounds embraced by Formula (II). In Scheme 2, 4-((aryl- or alkyl-oxy)carbonyl) piperazin-2-one 2-1 is alkylated with benzyl bromide 2-2 in the presence of a base (e.g., LiHMDS, NaHMDS, or NaH) to afford 1-benzyl-4-((aryl- or alkyl-oxy)carbonyl)piperazin-2-one 2-3, which can be deprotected by standard methods (e.g., treatment with hydrogen) to afford 1-benzylpiperazin-2-one 2-4. Benzylpiperazinone 2-4 can then be reacted with dialkylethoxymethylenemalonate 2-5 in a suitable solvent (e.g., a hydrocarbon such as toluene) at elevated temperature (e.g., from about 60 to about 90° C.) to afford the 2,2-dialkyloxy-carbonylethenyl-substituted product 2-6. Compound 2-6 can then be treated with a deprotonating agent (e.g., LiHMDS) in an aprotic solvent (e.g., DMF) to provide the alkyl 2-benzyl-8-hydroxy-1-oxo-1,2,3,4-tetrahydropyrrolopyrazine-7-carboxylate 2-7. Carboxylate 2-7 can be converted to the corresponding acid 2-8 by hydrolysis (e.g., with NaOH) and to the corresponding amide by treatment with an amine in the presence of a Lewis base (e.g., $AlCl_3$).

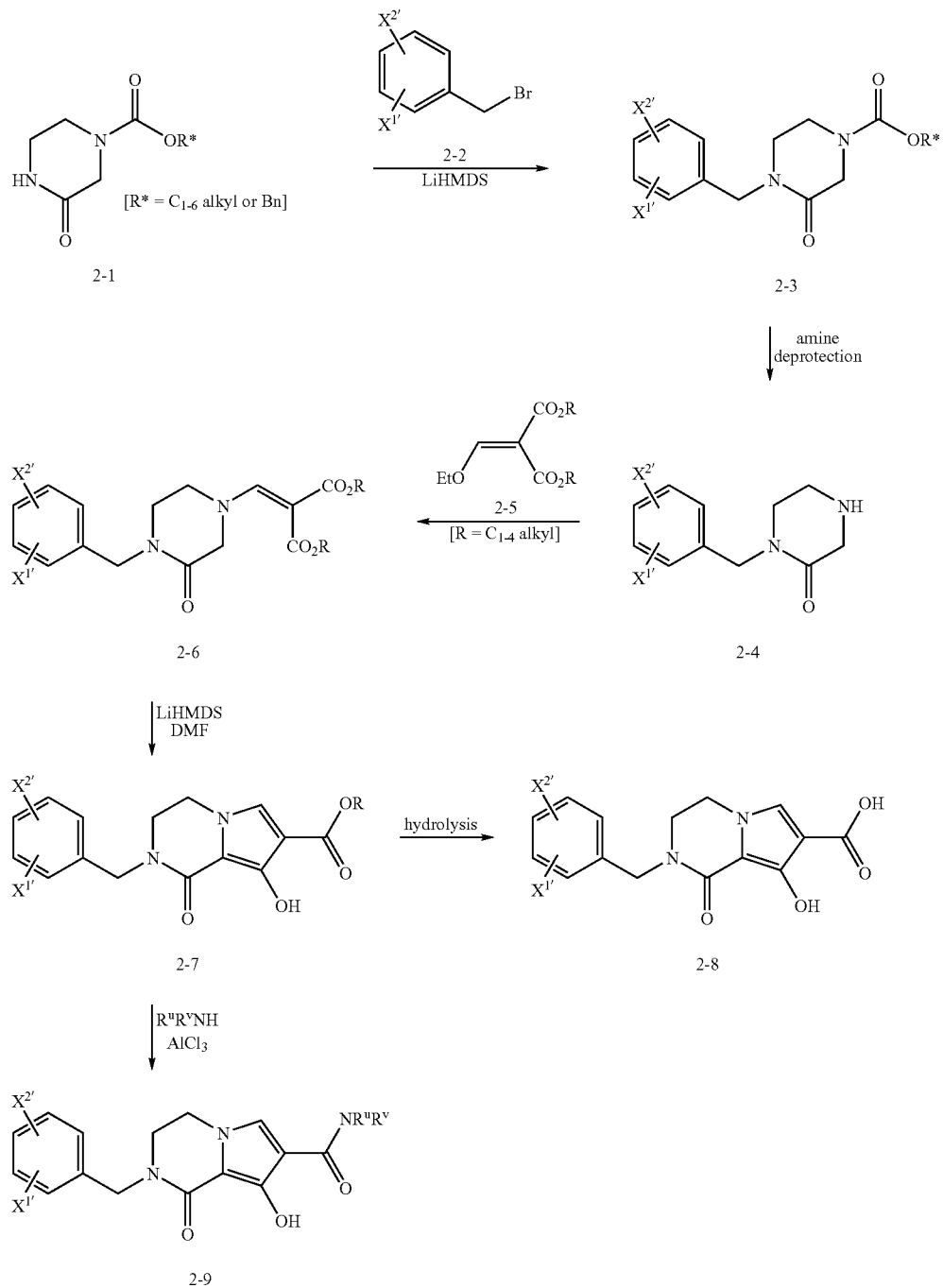

Scheme 3 illustrates a method for preparing compounds of Formula (IV).

Scheme 4 is a variation of Scheme 3 and exemplifies the preparation of compounds of Formula (IV) with $R^Z$=H. In Scheme 4, the piperazin-2-one 4-2 can be obtained by treatment of amine-protected piperazin-2-one 4-1 with base (e.g., LiHMDS, NaHMDS, or NaH) in DMF, followed by addition of methoxymethyl chloride or similar amide protecting group. Selective deprotection of the amine protecting group by hydrogenolysis provides piperazin-2-one 4-3. Treatment of piperazin-2-one 4-3 with dialkylalkoxymethylenemalonate 1-4 and then with a deprotonating agent provides 8-hydroxy-1-oxo-1,2,3,4-tetrahydropyrrolopyrazine-7-carboxylate 4-5. The carboxylate 4-5 can be hydrolyzed to give the 7-carboxylic acid 4-6, and deprotected to provide 4-7. Carboxylate 4-5 can also be treated with amine to give the 7-carboxamide 4-8, and deprotected to provide 4-9.

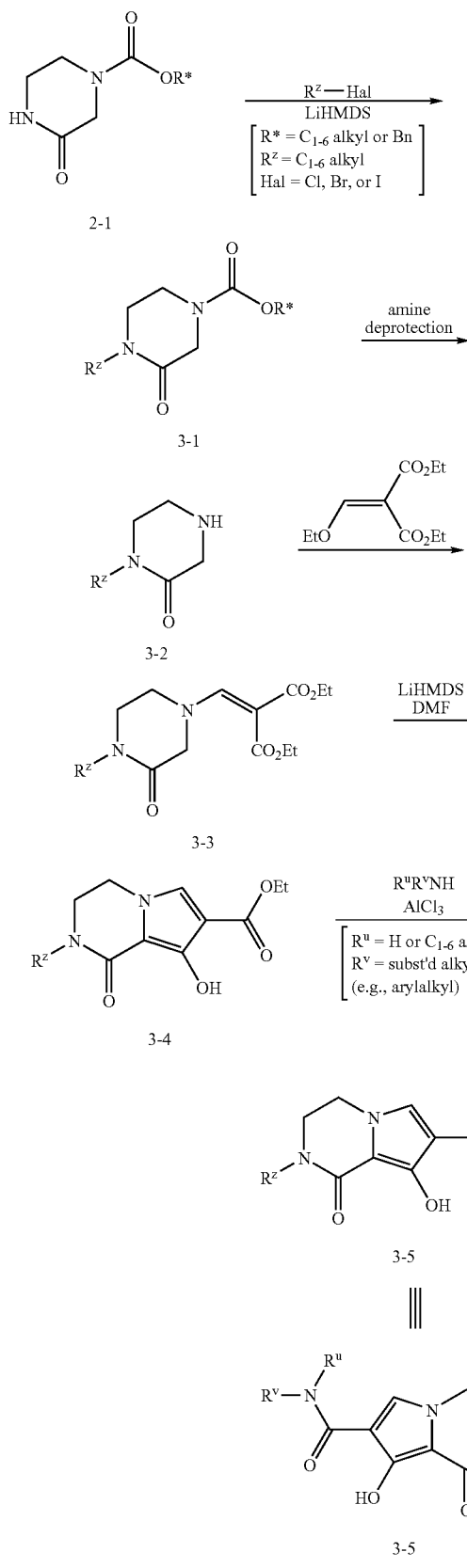

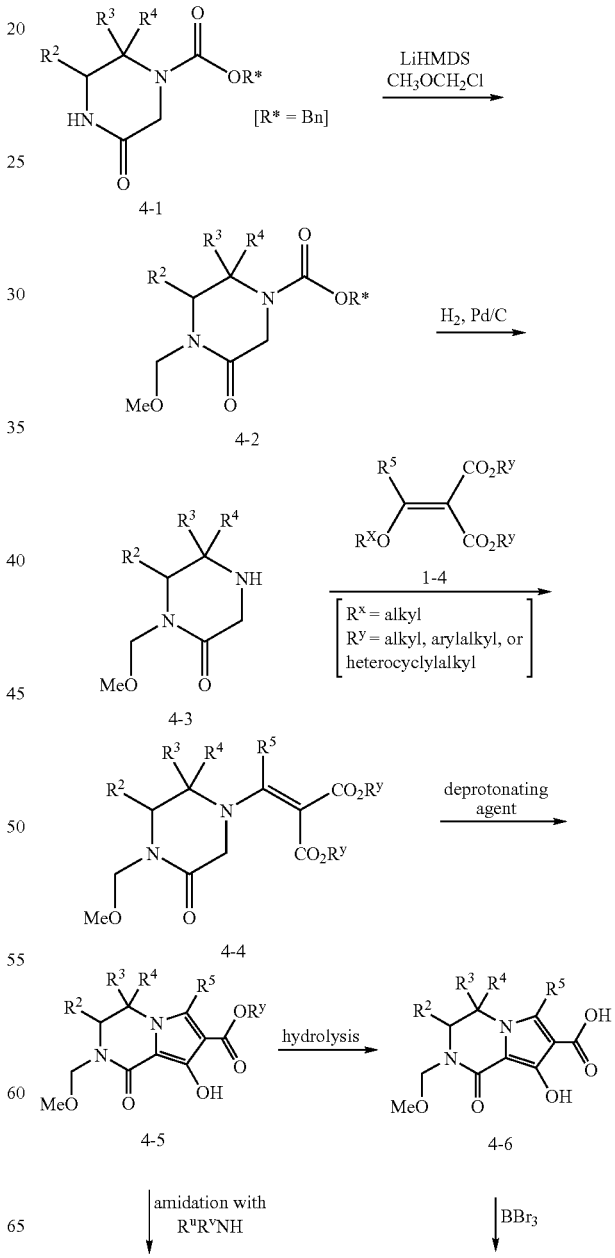

-continued

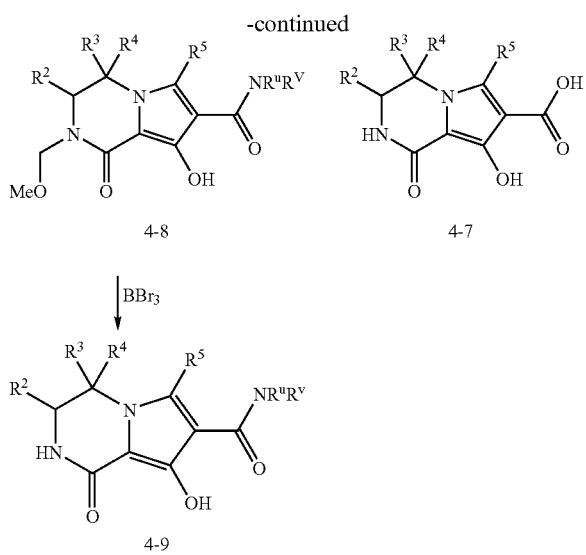

In the processes for preparing compounds of the present invention set forth in the foregoing schemes, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*. John Wiley & Sons, 1991. The protective groups may be removed at a convenient subsequent stage using methods known in the art. The use of protective groups is illustrated in Scheme 4.

The following examples serve only to illustrate the invention and its practice. The examples are not to be construed as limitations on the scope or spirit of the invention.

EXAMPLE 1

Ethyl 2-benzyl-8-hydroxy-1-oxo-1,2,3,4-tetrahydropyrrolo[1,2-α]pyrazine-7-carboxylate

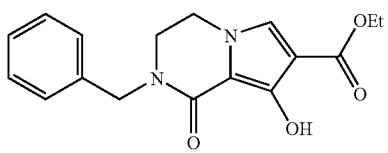

Step 1: Benzyl 4-benzyl-3-oxopiperazine-1-carboxylate

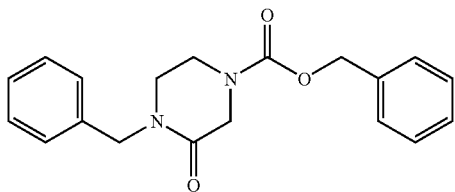

To a cold (0° C.) solution of benzyl 3-oxopiperazine-1-carboxylate (4.7 g, 20 mmol) in DMF (75 mL) under an atmosphere of nitrogen, a solution of lithium bis(trimethylsilyl)amide in THF (24 mL, 24 mmol) was added and stirred at the temperature for 30 min. The resultant solution was treated with benzyl bromide (2.9 mL, 24 mmol), and stirred at room temperature overnight. The product mixture was concentrated under vacuum, and the residue partitioned between aqueous HCl and ethyl acetate. The organic extracted was washed with brine, dried over anhydrous magnesium sulfate, filtered, and concentrated under vacuum. The residue was subjected to column chromatography on silica gel eluting with a 50-50 mixture of ethyl acetate and hexane. Collection and concentration of appropriate fractions provided the benzylated product.

$^1$H NMR (400 MHz, CDCl$_3$) δ7.4-7.2 (m, 10H), 5.15 (s, 2H), 4.63 (s, 2H), 4.25 (s, 2H), 3.66 (br t, J=5.3 Hz, 2H), 3.27 (br s, 2H).

ES MS M+1=325

Step 2: 1-Benzylpiperazin-2-one

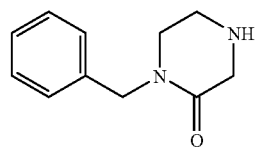

A mixture of benzyl 4-benzyl-3-oxopiperazine-1-carboxylate (4.7 g, 14.5 mmol) and 10% Pd/C (0.47 g) in ethanol (150 mL) was stirred under an atmosphere of hydrogen (1 atm) at room temperature overnight. The product mixture was filtered through a pad of Celite, and concentrated under vacuum to provide 1-benzylpiperazin-2-one.

$^1$H NMR (400 MHz, CDCl$_3$) δ 7.4-7.2 (m, 5M, 4.61 (s, 2H), 3.60 (s, 2H), 3.22 (t, J=5.3 Hz, 2H), 3.03 (t, J=5.3 Hz, 2H).

ES MS M+1=191

Step 3: Ethyl 2-benzyl-8-hydroxy-1-oxo-1,2,3,4-tetrahydropyrrolo[1,2-α]-pyrazine-7-carboxylate A mixture of 1-benzylpiperazin-2-one (0.29 g, 1.54 mmol) and diethyl ethoxymethylenemalonate (0.35 g, 1.63 mmol) in toluene was heated in a sealed tube at 80° C. for 4 hours. The resultant mixture was concentrated under vacuum. The residue was dissolved in anhydrous DMF (10 mL), cooled to 0° C. under an atmosphere of nitrogen, and treated with a solution of lithium bis(trimethylsilyl)amide in THF (1 M, 2.0 mL, 2.0 mmol). The reaction mixture was stirred at room temperature overnight and concentrated under vacuum. The residue was partitioned between ethyl acetate and dilute aqueous HCl. The organic extract was washed with brine, dried over anhydrous magnesium sulfate, filtered, and concentrated under vacuum. The residue was triturated with diethyl ether, and the solid precipitated was filtered to provide the title compound.

$^1$H NMR (400 MHz, CDCl$_3$) δ 8.39 (br s, 1H), 7.36-7.27 (m, 5H), 7.03 (s, 1H), 4.67 (s, 2H), 4.31 (q, J=7.1 Hz, 2H), 4.00 (t, J=5.8 Hz, 2H), 3.51 (t, J=5.8 Hz, 2H), 1.35 (t, J=7.1 Hz, 3H).

ES MS M+1=315

EXAMPLE 2

2-Benzyl-8-hydroxy-1-oxo-1,2,3,4-tetrahydropyrrolo[1,2-α]pyrazine-7-carboxylic acid

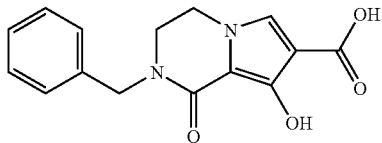

A mixture of ethyl 2-benzyl-8-hydroxy-1-oxo-1,2,3,4-tetrahydropyrrolo-[1,2-α]pyrazine-7-carboxylate (0.30 g; see Example 1) and aqueous sodium hydroxide (1 M, 2 mL) in ethanol (20 mL) was heated in a sealed tube at 100° C. overnight. The product mixture was acidified with addition of TFA and concentrated under vacuum. The residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-$d_6$) δ 7.37-7.25 (m, 6H), 4.62 (s, 2H), 4.09 (t, J=5.7 Hz, 2H), 3.52 (t, J=5.7 Hz, 2H).

ES MS M+1=287

EXAMPLE 3

Ethyl 2-(4-fluorobenzyl)-8-hydroxy-1-oxo-1,2,3,4-tetrahydropyrrolo[1,2-]pyrazine-7-carboxylate

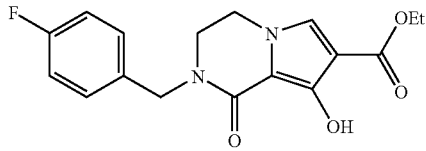

The title compound was prepared using a procedure similar to that described in Example 1, except that benzyl bromide (Step 1) was substituted with 4-fluorobenzyl bromide.

$^1$H NMR (400 MHz, DMSO-$d_6$) δ 8.54 (s, 1H), 7.40 (dd, J=8.3, 5.8 Hz, 2H), 7.36 (s, 1H), 7.17 (t, J=8.3 Hz, 2H), 4.59 (s, 2H), 4.18 (q, J=7.1 Hz, 2H), 4.01 (t, J=5.3 Hz, 2H), 3.53 (t, J=5.3 Hz, 2H), 1.24 (t, J=7.1 Hz, 3H).

ES MS M+1=333

EXAMPLE 4

2-(4-Fluorobenzyl)-8-hydroxy-1-oxo-1,2,3,4-tetrahydropyrrolo[1,2-α]pyrazine-7-carboxylic acid

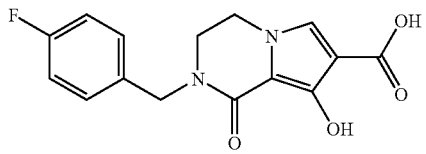

The title compound was prepared using a procedure similar to that described in Example 2, except that ethyl 2-benzyl-8-hydroxy-1-oxo-1,2,3,4-tetrahydropyrrolo-[1,2-α]pyrazine-7-carboxylate was substituted wit ethyl 2-(4-fluorobenzyl)-8-hydroxy-1-oxo-1,2,3,4-tetrahydropyrrolo[1,2-α]pyrazine-7-carboxylate.

$^1$H NMR (400 MHz, DMSO-$d_6$) δ 8.6 (br s, 1H), 7.40 (dd, J=8.3, 5.8 Hz, 2H), 7.31 (s, 1H), 7.36 (s, 1H), 7.17 (t, J=8.3 Hz, 2H), 4.59 (s, 2H), 4.09 (t, J=5.5 Hz, 2H), 3.52 (t, J=5.5 Hz, 2H).

ES MS M+1=305

EXAMPLE 5

2-(4-Fluorobenzyl)-8-hydroxy-N-methyl-1-oxo-1,2,3,4-tetrahydropyrrolo[1,2α]pyrazine-7-carboxamide

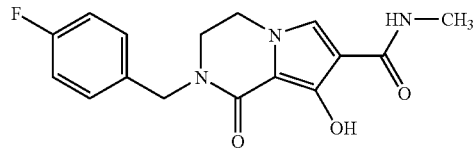

Anhydrous methylamine gas was bubbled through a mixture of ethyl 2-(4-fluorobenzyl)-8-hydroxy-1-oxo-1,2,3,4-tetrahydropyrrolo[1,2-α]pyrazine-7-carboxylate (200 mg) and anhydrous aluminum chloride (200 mg) in anhydrous chloroform at 0° C. for 5 minutes. The resistant mixture was heated in a seal tube at 70° C. overnight and concentrated under vacuum. The residue was dissolved in DMSO and acidified with TFA. The solution was subjected to HPLC purification on C-18 stationary phase eluted with water/acetonitrile/ TFA mobile phase. Collection and lyophilization of appropriate fractions provided the title compound.

$^1$H NMR (400 MHz, DMSO-$d_6$) δ 7.71 (br q, J=4.6, 1H), 7.35 (dd, J=8.6, 5.7 Hz, 2H), 7.24 (s, 1H), 7.17 (t, J=8.6 Hz, 2H), 4.59 (s, 2M), 4.07 (t, J=5.3 Hz, 2H), 3.50 (t, J=5.2 Hz, 2H), 2.74 (s, 3H).

ES MS M+1=318

EXAMPLE 6

2-(2-Fluorobenzyl)-8-hydroxy-N-ethyl-1-oxo-1,2,3,4-tetrahydropyrrolo[1,2-α]pyrazine-7-carboxamide

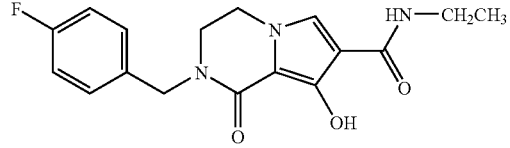

The title compound was prepared using a procedure similar to that described in Example 5, except that methylamine was substituted with ethylamine.

$^1$H NMR (400 MHz, DMSO-$d_6$) δ 7.76 (br t, J=53, 1H), 7.35 (dd, J=8.7, 5.6 Hz, 2H), 7.27 (s 1H), 7.17 (t, J=8.8 Hz, 2H), 4.59 (s, 2H), 4.07 (t, J=5.9 Hz, 2H), 3.50 (t, J=5.9 Hz, 2H), 3.25 (m, 2H), 1.09 (t, J=7.1 Hz, 3H).

ES MS M+1=332

EXAMPLE 7

2-(4Fluorobenzyl)-8-hydroxy-N-cyclopropyl-1-oxo-1,2,3,4-tetrahydropyrrolo[1,2α]pyrazine-7-carboxamide

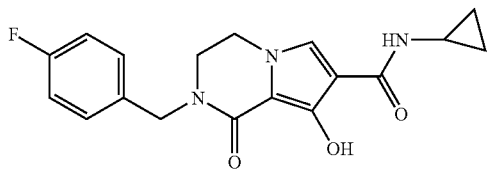

The title compound was prepared using a procedure similar to that described in Example 5, except that methylamine was substituted with cyclopropyl amine.

$^1$H NMR (400 MHz, DMSO-$d_6$) δ 7.76 (br d, J=3.2, 1H), 7.35 (dd, J=8.2, 5.6 Hz, 2H), 7.26 (s 1H), 7.17 (t, J=8.9 Hz, 2H), 4.59 (s, 2H), 4.06 (t, J=5.9 Hz, 2H), 3.50 (t, J=5.9 Hz, 2H), 2.75 (m, 1H), 0.69 (m, 2H), 0.49 (m, 2H).

ES MS M+1=344

EXAMPLE 8

Ethyl 2(3-chlorobenzyl)-8-hydroxy-1-oxo-1,2,3,4-tetrahydropyrrolo[1,2-α]pyrazine-7-carboxylate

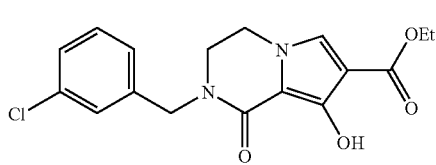

Step1; 1-(3-chlorobenzyl)piperazin-2-one

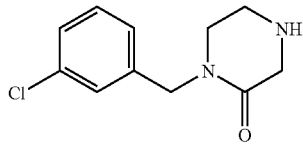

To a cold (0° C.) solution of 4-[(tert-butoxy)carbonyl]-piperazin-2-one (4.0 g, 20 mmol) in DMF (175 mL) under an atmosphere of nitrogen, a solution of lithium bis(trimethylsilyl)amide in THF (22 mL, 22 mmol) was added and stilled at the temperature for 30 min. The resultant solution was treated with 3-chlorobenzyl bromide (2.6 mL, 20 mmol), and stirred at room temperature overnight. The product mixture was concentrated under vacuum, and the residue partitioned between 0.1 M aqueous HCl and ethyl acetate. The organic extracted was washed with brine, dried over anhydrous magnesium sulfate, filtered, and concentrated under vacuum. The residue was subjected to column chromatography on silica gel eluting with a 50-50 mixture of ethyl acetate and hexane Collection and concentration of appropriate fractions provided the benzylated product The product was dissolved in ethyl acetate (150 mL) and cooled to 0° C. A steady steam of anhydrous HCl gas was bubbled through for 10 minutes. The resultant mixture was capped and stirred at the same temperature for 1 hour. The product mixture was concentrated under vacuum. The residue was treated with chloroform saturated with ammonia, and the resultant suspension was filtered through a pad of Celite. The filtrate was concentrated under vacuum provided the title amine. Residual ammonia was removed by concentrating the residue three time with toluene under vacuum

ES MS M+1=225

Step 2: Ethyl 2-(3-chlorobenzyl)-8-hydroxy-1-oxo-1,2,3,4-tetrahydropyrrolo[1,2-α]-pyrazine-7-carboxylate A mixture of 1-(3-chlorobenzyl)piperazin-2-one (3.97 g, 17.67 mmol) and diethyl ethoxymethylenemalonate (4.01 g, 18.55 mmol) in toluene (60 mL) was heated in a sealed tube at 80° C. overnight. The resultant mixture was concentrated under vacuum. The residue was dissolved in anhydrous DMF (200 mL), cooled to 0° C. under an atmosphere of nitrogen, and treated with a solution of lithium bis(trimethylsilyl)amide in THF (1 M, 21.2 mL, 21.2 mmol). The reaction mixture was stirred at room temperature overnight and concentrated under vacuum. The residue was partitioned between ethyl acetate and dilute aqueous HCl. The organic extract was washed with brine, dried over anhydrous magnesium sulfate, filtered, and concentrated under vacuum. The residue was triturated with diethyl ether, and the solid precipitated was filtered to provide the title compound.

$^1$H NMR (400 MHz, DMSO-$d_6$) δ 8.60 (s, 1H), 7.41-7.28 (m, 5H), 4.62 (s, 2H), 4.19 (q, J=7.2 Hz, 2H), 4.11 (t, J=5.9 Hz, 2H), 3.57 (t, J=5.9 Hz, 2H), 1.25 (t, J=7.2 Hz, 3H).

ES MS M+1=349

EXAMPLE 9

2-(3-Chlorobenzyl)-8-hydroxy-1-oxo-1,2,3,4-tetrahydropyrrolo[1,2-α]pyrazine-7-carboxylic acid

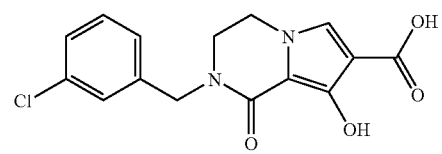

The title compound was prepared using a procedure similar to that described in Example 2, except that ethyl 2-benzyl-8-hydroxy-1-oxo-1,2,3,4-tetrahydropyrrolo-[1,2-α]pyrazine-7-carboxylate was substituted with ethyl 2-(3-chlorobenzyl)-8-hydroxy-1-oxo-1,2,3,4-tetrahydropyrrolo[1,2-α]pyrazine-7-carboxylate.

$^1$H NMR (400 MHz, DMSO-$d_6$) δ 12.33 (br s, 1H), 8.69 (br s, 1H), 7.41-7.27 (m, 5H), 4.61 (s, 2H), 4.10 (t, J=5.3 Hz, 2H), 3.55 (t, J=5.3 Hz, 2H).

ES MS M+1=322

EXAMPLE 10

N-(4-Fluorobenzyl)-8-hydroxy-2-methyl-1-oxo-1,2,3,4-tetrahydropyrrolo[1,2-α]pyrazine-7-carboxamide

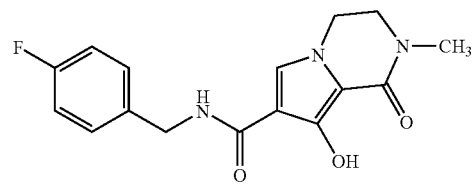

Step 1: 1-Methylpiperazin-2-one

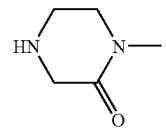

The title compound was prepared using a procedure similar to that described in Example 1 (Step 1 & 2), except that benzyl bromide (Step 1) was substituted with methyl iodide.

ES MS M+1=115

Step 2: Ethyl 8-hydroxy-2-methyl-1-oxo-1,2,3,4-tetrahydro-pyrrolo[1,2-α]pyrazine-7-carboxylate

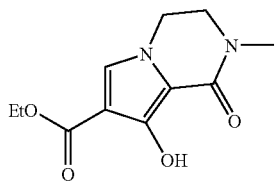

The title compound was prepared using a procedure similar to that described in Example 1 (Step 3), except that 1-benzylpiperazin-2-one was substituted with 1-methylpiperazin-2one.

ES MS M+1=238

Step 3: N-(4-Fluorobenzyl)-8-hydroxy-2-methyl-1-oxo-1,2,3,4-tetrahydro-pyrrolo[1,2-α]pyrazine-7-carboxamide The tile compound was prepared using a procedure similar to that described in Example 5, except that methylamine was substituted with 4-fluorobenzyl-amine.

ES MS M+1=318

EXAMPLE 11

Ethyl 2-(3-fluorobenzyl)-8-hydroxy-1-oxo-1,2,3,4-tetrahydropyrrolo[1,2-α]pyrazine-7-carboxylate

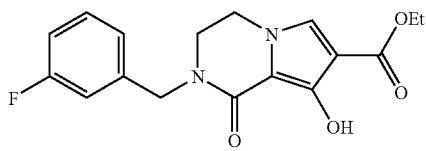

The title compound was prepared using a procedure similar to that described in Example 1, except that benzyl bromide (Step 1) was substituted with 3-fluorobenzyl bromide.

$^1$H NMR (400 MHz, DMSO-d$_6$) δ 7.36 (dd, J=8, 8 Hz, 1H), 7.2-6.8 (m, 5 H), 4.57 (s, 2H), 4.05 (q, J=7.1 Hz, 2H), 4.01 (t, J=5.3 Hz, 2H), 3.53 (t, J=5.3 Hz, 2H), 1.18 (t, J=7.1 Hz, 3H).

ES MS M+1=333

EXAMPLE 12

Ethyl 2(3,4-fluorobenzyl)-8-hydroxy-1-oxo-1,2,3,4-tetrahydropyrrolo[1,2-α]pyrazine-7-carboxylate

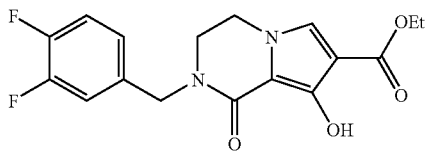

The title compound was prepared using a procedure similar to that described in Example 1, except that benzyl bromide (Step 1) was substituted with 3,4-difluorobenzyl bromide.

$^1$H NMR (400 MHz, DMSO-d$_6$) δ 7.43-6.82 (m, 5l), 4.58 (s, 2H), 4.18 (q, J=7.0 Hz, 2H), 4.02 (t, J=5.3 Hz, 2H), 3.52 (t, J=5.3 Hz, 2H), 1.23 (t, J=7.0 Hz, 3H).

ES MS M+1=351

EXAMPLE 13

Ethyl 2-(4-chlorobenzyl)-8-hydroxy-1-oxo-1,2,3,4-tetrahydropyrrolo[1,2-α]pyrazine-7-carboxylate

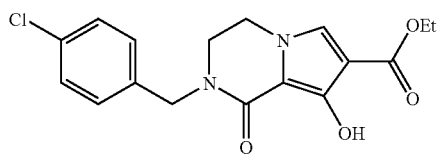

Step 1: tert-Butyl 4-(chlorobenzyl)-3-oxopiperazine-1-carboxylate

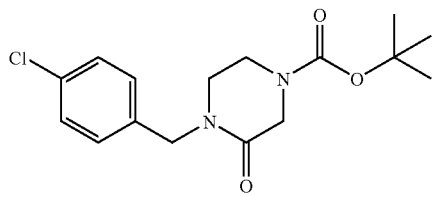

To a cold (0° C.) solution of tert-butyl 3-oxopiperazine-1-carboxylate (2.0 g, 9.9 mmol) in DMF (100 mL) under an atmosphere of nitrogen, a solution of lithium bis(trimethylsilyl)amide in THF (10.9 mL, 10.9 mmol) was added and stirred at the temperature for 30 min The resultant solution was treated with 4-chlorobenzyl bromide (2.1, 10.5 mmol), and stirred at room temperature overnight. The product mixture was concentrated under vacuum, and the residue partitioned between aqueous HCl and ethyl acetate. The organic extracted was washed with brine, dried over anhydrous magnesium sulfate, filtered, and concentrated under vacuum. The residue was subjected to column chromatography on silica gel eluting with a mixture of ethyl acetate and dichloromethane (0 to 50% gradient). Collection and concentration of appropriate fractions provided the benzylated product.

$^1$H NMR (400 MHz, CDCl$_3$) δ 7.31 (br d, J=8.5 H, 2H), 7.20 (br d, J=8.5 H, 2H), 4.58 (s, 2H), 4.15 (s, 2H), 3.59 (br t, J=5.3 Hz, 2H), 3.25 (br t, 2H).

ES MS M+1=325

Step 2: 1-(4Chlorobenzyl)-piperazin-2-one

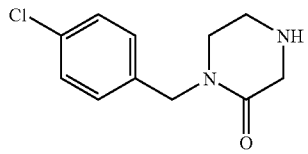

A cold (0° C.) solution of tert-Butyl 4-(4-chlorobenzyl)-3-oxopiperazine-1-carboxylate (3.2 g, 9.9 mmol) in ethyl acetate (100 mL) was saturated with HCl gas. The resultant mixture was stirred at 0° C. for 1 h. The product mixture was concentrated under vacuum. The residue was treated with dichloromethane saturated with ammonia gas. The resultant chalky mixture was filtered, and the filtrate concentrated under vacuum. The residue was diluted with benzene and concentrated under vacuum to provide 1-(4-chlorobenzyl)-piperazin-2-one.

ES MS M+1=225

Step 3: Ethyl 2-(4-chlorobenzyl)-8-hydroxy-1-oxo-1,2,3,4-tetrahydropyrrolo[1,2-α]pyrazine-7-carboxylate

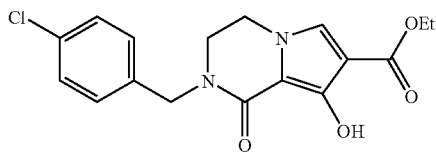

A mixture of 1-(4-chlorobenzyl)-piperazin-2-one (1.94 g, 8.63 mmol) and diethyl ethoxymethylenemalonate (1.87 g, 8.63 mmol) in toluene (40 mL) was heated in a sealed tube at 80° C. overnight The resultant mixture was concentrated under vacuum. The residue was dissolved in anhydrous DMF (50 mL), cooled to 0° C. under an atmosphere of nitrogen, and treated with a solution of lithium bis(trimethylsilyl)amide in THF (1 M, 12 mL, 12 mmol). The reaction mixture was stirred at room temperature overnight and concentrated under vacuum. The residue was partitioned between ethyl acetate and dilute aqueous HCl. The organic extract was washed with brine, dried over anhydrous magnesium sulfate, filtered, and concentrated under vacuum The residue was subjected to HPLC purification on C-18 stationary phase eluted with water/acetonitrile/TFA mobile phase. Collection and lyophilization of appropriate fractions provided the title compound.

$^1$H NMR (400 MHz, DMSO-$d_6$) δ 7.37 (d, J=8.3, 2H), 7.30 (d, J=8.3, 2H), 7.09 (s, 1H), 4.55 (s, 2H), 4.05 (q, J=7.1 Hz, 2H), 4.01 (br t, 2H), 3.53 (br t, 2H), 1.19 (t, J=7.1 Hz, 2H).
ES MS M+1=349

EXAMPLE 14

Ethyl 2-(3-chloro-4-fluorobenzyl)-8-hydroxy-1-oxo-1,2,3,4-tetrahydropyrrolo[1,2-α]pyrazine-7-carboxylate

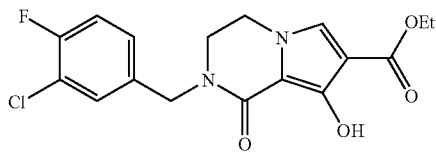

The title compound was prepared using a procedure similar to that described in Example 13, except that 4-chlorobenzyl bromide (Step 1) was substituted with 3-chloro-4-fluorobenzyl bromide.

$^1$H NMR (400 MHz, DMSO-$d_6$) δ 8.58 (s, 1H), 7.4-7.3 (m, 4 H), 4.59 (s, 2H), 4.18 (q, J=7.1 Hz, 2H), 4.11 (t, J=5.3 Hz, 2H), 3.56 (t, J=5.3 Hz, 2H), 1.24 (t, J=7.1 Hz, 2H),
ES MS M+1=367

EXAMPLE 15

Ethyl 2-(3,4-dichlorobenzyl)-8-hydroxy-1-oxo-1,2,3,4-tetrahydropyrrolo[1,2-α]pyrazine-7-carboxylate

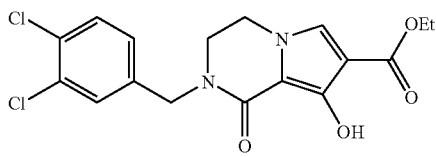

The title compound was prepared using a procedure similar to that described in Example 13, except that 4-chlorobenzyl bromide (Step 1) was substituted with 3,4-dichlorobenzyl bromide.

$^1$H NMR (400 MHz, DMSO-$d_6$) δ 8.59 (s, 1H), 7.61 (d, J=8.4 Hz, 1H), 7.58 (d, J=1.8 Hz, 1H), 7.37 (s, 1H), 7.31 (dd, J=8.4, 1.8 Hz, 1H), 4.60 (s, 2H), 4.18 (q, J=7.0 Hz, 2H), 4.11 (t, J=5.8 Hz, 2H), 3.57 (t, J=5.8 Hz, 2H), 1.24 (t, J=7.0 Hz, 3H).
ES MS M+1=383

EXAMPLE 16

2-(4-Chlorobenzyl)-8-hydroxy-N-methyl-1-oxo-1,2,3,4-tetrahydropyrrolo[1,2-α]pyrazine-7-carboxamide

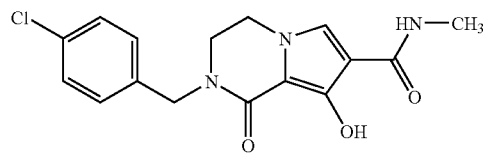

The title compound was prepared using a procedure similar to that described in Example 5, except that ethyl 2-(4-fluorobenzyl)-8-hydroxy-1-oxo-1,2,3,4-tetrahydropyrrolo[1,2-α]pyrazine-7-carboxylate was substituted with ethyl 2-(4-chlorobenzyl)-8-hydroxy-1-oxo-1,2,3,4-tetrahydropyrrolo[1,2-α]pyrazine-7-carboxylate (Example 13).

$^1$H NMR (400 MHz, CDCl$_3$) δ 7.33 (d, J=8.2, 1H), 7.27-7.21 (m), 7.18 (s, 1H), 4.65 (s, 2H), 4.03 (t, J=6.3 Hz, 2H), 3.53 (t, J=6.3 Hz, 2H), 2.99 (d, J=4.8 Hz, 3H).
ES MS M+1=334

EXAMPLE 17

2-(3,4-Difluorobenzyl)-8-hydroxy-N-methyl-1-oxo-1,2,3,4-tetrahydropyrrolo[1,2-α]pyrazine-7-carboxamide

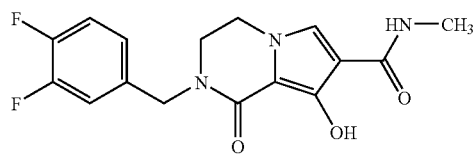

The title compound was prepared using a procedure similar to that described in Example 5, except that ethyl 2-(4-fluorobenzyl)-8-hydroxy-1-oxo-1,2,3,4-tetrahydropyrrolo[1,2-α]pyrazine-7-carboxylate was substituted with ethyl 2-(3,4-difluorobenzyl)-8-hydroxy-1-oxo-1,2,3,4-tetrahydropyrrolo[1,2-α]pyrazine-7-carboxylate (Example 12).

$^1$H NMR (400 MHz, CDCl$_3$) δ 7.34-7.05 (m), 6.74 (br s, 1H), 4.64 (s, 2H), 4.05 (t, J=5.7 Hz, 2H), 3.54 (t, J=57 Hz, 2H), 2.99 (d, J=4.6 Hz, 3H).
ES MS M+1=336

EXAMPLE 18

2-(3,4-Dichlorobenzyl)-8-hydroxy-N-methyl-1-oxo-1,2,3,4-tetrahydropyrrolo[1,2-α]pyrazine-7-carboxamide

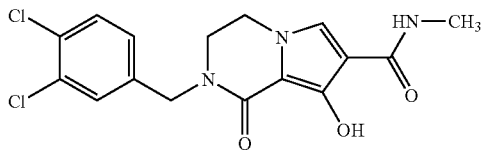

The title compound was prepared using a procedure similar to that described in Example 5, except that ethyl 2-(4-fluorobenzyl)-8-hydroxy-1-oxo-1,2,3,4-tetrahydropyrrolo[1,2-α]pyrazine-7-carboxylate was substituted with ethyl 2-(3,4-dichlorobenzyl)-8-hydroxy-1-oxo-1,2,3,4-tetrahydropyrrolo[1,2-α]pyrazine-7-carboxylate (Example 15).

$^1$H NMR (400 MHz, CDCl$_3$) δ 7.43 (d, J=8.4 Hz, 1H), 7.40 (d, J=1.8 Hz, 1H), 7.19 (s, 1H), 7.16 (dd, J=8.4, 1.8 Hz, 1H), 4.64 (s, 2H), 4.05 (t, J=5.7 Hz, 2H), 3.54 (t, J=5.7 Hz, 2H), 2.99 (d, J=4.6 Hz, 3H).

ES MS M+1=368

EXAMPLE 19

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2-18 can be similarly prepared.

EXAMPLE 20

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds prepared in Examples 1-18 were tested in the integrase assay and all were found to have IC$_{50}$'s less than 1.5 micromolar In particular, the compounds prepared in Examples 1-10 were all found to have IC$_{50}$'s less than 0.7 micromolar in the integrase assay.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 21

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds prepared in Examples 1, 3, 5-8, 10, 16 and 17 were found to have IC$_{95}$'s at or less than 20 micromolar in the present assay.

While the foregoing specification teaches the principles of the present invention, with examples provided for the purpose of illustration, the practice of the invention encompasses all of the usual variations, adaptations and/or modifications that come within the scope of the following claim.

What is claimed is:

1. A compound of Formula (I), or a pharmaceutically acceptable salt thereof:

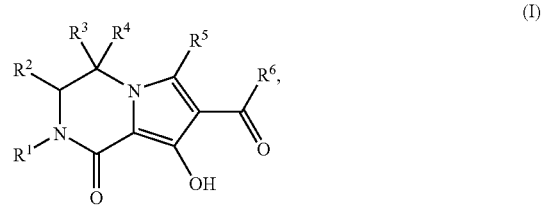

wherein
R$^1$ is —H, —C$_{1-6}$ alkyl, —C$_{3-6}$ cycloalkyl, or —C$_{1-6}$ alkyl which is substituted with 1 or 2 substituents each of which is independently:
(1) C$_{3-8}$ cycloalkyl,
(2) aryl,
(3) a 5- or 6-membered saturated or mono-unsaturated heterocyclic ring containing from 1 to 4 heteroatoms independently selected from N, O and S,
(4) a 5- or 6-membered heteroaromatic ring containing from 1 to 4 heteroatoms independently selected from N, O and S, or
(5) a 9- or 10-membered fused bicyclic heterocycle containing from 1 to 4 heteroatoms independently selected from N, O and S, wherein at least one of the rings is aromatic;
wherein
(A) each cycloalkyl is optionally substituted with from 1 to 3 substituents, each of which is independently halo, —C$_{1-6}$ alkyl, or —O—C$_{1-6}$ alkyl;
(B) each aryl is optionally substituted with from 1 to 5 substituents each of which is independently
(1) —C$_{1-6}$ alkyl, optionally substituted with from 1 to 3 substituents each of which is independently —OH, —O—C$_{1-6}$ alkyl, —O—C$_{1-6}$ haloalkyl, —CN, —NO$_2$, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
(2) —O—C$_{1-6}$ alkyl, optionally substituted with from 1 to 3 substituents each of which is independently —OH, —O—C$_{1-6}$ alkyl, —O—C$_{1-6}$ haloalkyl, —S(O)$_n$R$^c$, —C(=O)N(R$^a$R$^b$), —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
(3) —C$_{1-6}$ haloalkyl,
(4) —O—C$_{1-6}$ haloalkyl,
(5) —OH,
(6) halo,
(7) —CN,
(8) —NO$_2$,
(9) —N(R$^a$R$^b$),
(10) —C(=O)N(R$^a$R$^b$),
(11) —C(=O)R$^a$,
(12) —CO$_2$R$^c$,
(13) —SR$^c$,

(14) —S(=O)R$^c$,
(15) —SO$_2$R$^c$,
(16) —N(R$^a$)SO$_2$R$^c$,
(17) —SO$_2$N(R$^a$R$^b$),
(18) —N(R$^a$)C(=O)R$^b$, or
(19) —N(R$^a$)CO$_2$R$^c$;

(C) each saturated or mono-unsaturated heterocyclic ring is
  (i) optionally substituted with from 1 to 5 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; and
  (ii) optionally substituted with 1 or 2 substituents each of which is independently aryl or a 5- or 6-membered heteroaromatic ring containing from 1 to 4 heteroatoms independently selected from N, O and S; and (D) each heteroaromatic ring or each fused bicyclic heterocycle is
  (i) optionally substituted with from 1 to 7 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; and
  (ii) optionally substituted with 1 or 2 substituents each of which is independently aryl or —C$_{1-6}$ alkyl-aryl;

R$^2$ is —H or —C$_{1-6}$ alkyl;

R$^3$ is —H, —C$_{1-6}$ alkyl, —C$_{1-6}$ haloalkyl, or —C$_{1-6}$ alkyl substituted with one of —OH, —O—C$_{1-6}$ alkyl, —O—C$_{1-6}$ haloalkyl, —CN, —NO$_2$, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$);

R$^4$ is:
  (1) —H,
  (2) —C$_{1-6}$ alkyl optionally substituted with one of —OH, —O—C$_{1-6}$ alkyl, —O—C$_{1-6}$ haloalkyl, —CN, —NO$_2$, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)—C(R$^b$)=O, —N(R$^a$)SO$_2$R$^c$, —N(R$^a$)SO$_2$N(R$^a$R$^b$), —OC(=O)N(R$^a$R$^b$), —N(R$^a$)C(=O)N(R$^a$R$^b$), —O—C$_{1-6}$ alkyl-C(=O)N(R$^a$R$^b$), —S—C$_{1-6}$ alkyl-C(=O)N(R$^a$R$^b$), —N(R$^a$)—C$_{1-6}$ alkyl-C(=O)N(R$^a$R$^b$), or —N(SO$_2$R$^c$)—C$_{1-6}$ alkyl-C(=O)N(R$^a$R$^b$),
  (3) —C$_{1-6}$ haloalkyl,
  (4) —C(=O)R$^a$,
  (5) —CO$_2$R$^c$,
  (6) —C(=O)N(R$^a$R$^b$),
  (7) —SO$_2$N(R$^a$R$^b$),
  (8) —C$_{2-6}$ alkenyl,
  (9) —C$_{2-6}$ alkenyl-C(=O)—N(R$^a$)$_2$,
  (10) —C$_{2-5}$ alkynyl,
  (11) —C$_{2-5}$ alkynyl-CH$_2$N(R$^a$)$_2$,
  (12) —C$_{2-5}$ alkynyl-CH$_2$OR$^a$,
  (13) —C$_{2-5}$ alkynyl-CH$_2$S(O)$_n$R$^c$, or
  (14) —R$^k$,
  (15) —C$_{1-6}$ alkyl substituted with R$^k$,
  (16) —C$_{1-6}$ haloalkyl substituted with R$^k$,
  (17) —C$_{1-6}$ alkyl-O—R$^k$,
  (18) —C$_{1-6}$ alkyl-O—C$_{1-6}$ alkyl-R$^k$,
  (19) —C$_{1-6}$ alkyl-S(O)$_n$—R$^k$,
  (20) —C$_{1-6}$ alkyl-S(O)$_n$—C$_{1-6}$ alkyl-R$^k$,
  (21) —C$_{1-6}$ alkyl-N(R$^a$)—R$^k$,
  (22) —C$_{1-6}$ alkyl-N(R$^a$)—C$_{1-6}$ alkyl-R$^k$,
  (23) —C$_{1-6}$ alkyl-N(R$^a$)—C$_{1-6}$ alkyl-OR$^k$, with the proviso that the —N(R$^a$)— moiety and the —OR$^k$ moiety are not both attached to the same carbon of the —C$_{1-6}$ alkyl-moiety,
  (24) —C$_{1-6}$ alkyl-C(=O)—R$^k$,
  (25) —C$_{1-6}$ alkyl-C(=O)N(R$^a$)—R$^k$,
  (26) —C$_{1-6}$ alkyl-N(R$^a$)C(=O)—R$^k$,
  (27) —C$_{1-6}$ alkyl-C(=O)N(R$^a$)—C$_{1-6}$ alkyl-R$^k$, or
  (28) —C$_{1-6}$ alkyl-N(R$^a$)—C$_{0-6}$ alkly-S(O)$_n$R$^k$;
  wherein R$^k$ is
  (i) aryl, which is optionally substituted with from 1 to 5 substituents each of which is independently —C$_{1-6}$ alkyl, —C$_{1-6}$ alkyl-OH, —C$_{1-6}$ alkyl-O—C$_{1-6}$ alkyl, —C$_{1-6}$ alkyl-O—C$_{1-6}$ haloalkyl, —C$_{1-6}$ alkyl-N(R$^a$R$^b$), —C$_{1-6}$ alkyl-C(=O)N(R$^a$R$^b$), —C$_{1-6}$ alkyl-C(=O)R$^a$, —C$_{1-6}$ alkyl-CO$_2$R$^c$, —C$_{1-6}$ alkyl-S(O)$_n$R$^c$, —O—C$_{1-6}$ alkyl, —C$_{1-6}$ haloalkyl, —O—C$_{1-6}$ haloalkyl, —OH, halo, —N(R$^a$R$^b$), —C(=O)N(R$^a$R$^b$), —C(=O)R$^a$, —CO$_2$R$^c$, —S(O)$_n$R$^c$, or —SO$_2$N(R$^a$R$^b$);
  (ii) a 4- to 7-membered saturated or mono-unsaturated heterocyclic ring containing at least one carbon atom and from 1 to 4 heteroatoms independently selected from N, O and S, wherein the heterocyclic ring is:
    (a) optionally substituted with from 1 to 5 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; and
    (b) optionally mono-substituted with aryl or HetA; wherein HetA is a 5- or 6-membered heteroaromatic ring containing from 1 to 4 heteroatoms independently selected from N, O and S, wherein the heteroaromatic ring is optionally fused with a benzene ring, and HetA is optionally substituted with from 1 to 4 substituents each of which is independently —C$_{1-6}$ alkyl, —C$_{1-6}$ haloalkyl, —O—C$_{1-6}$ alkyl, —O—C$_{1-6}$ haloalkyl, or oxo; or
  (iii) a 5- or 6-membered heteroaromatic ring containing from 1 to 4 heteroatoms independently selected from N, O and S, wherein the heteroaromatic ring is optionally substituted with from optionally substituted with from 1 to 4 substituents each of which is independently —C$_{1-6}$ alkyl, —C$_{1-6}$ haloalkyl, —O—C$_{1-6}$ alkyl, —O—C$_{1-6}$ haloalkyl, or oxo;

R$^5$ is —H or —C$_{1-6}$ alkyl;

R$^6$ is:
  (1) —O—C$_{1-6}$ alkyl,
  (2) —N(R$^u$R$^v$),
  (3) —O—C$_{1-6}$ haloalkyl,
  (4) —O—C$_{1-6}$ alkyl-aryl
  (5) —O—C$_{1-6}$ alkyl-HetB, or
  (6) —O—C$_{1-6}$ alkyl-HetC,
  wherein
  R$^u$ is —H or —C$_{1-6}$ alkyl;
  R$^v$ independently has the same definition as R$^1$;
  HetB is a 5- or 6-membered saturated or mono-unsaturated ring containing from 1 to 4 heteroatoms independently selected from N, O and S, wherein the ring is optionally substituted with from 1 to 5 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; and
  HetC is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo;

each $R^a$ and $R^b$ is independently —H or —$C_{1-6}$ alkyl;

each $R^c$ is independently a —$C_{1-6}$ alkyl; and each n is independently an integer equal to 0, 1 or 2.

2. The compound according to claim 1, or a pharmaceutically acceptable salt thereof, wherein:

$R^1$ is —$C_{1-4}$ alkyl mono-substituted with aryl; wherein the aryl is optionally substituted with from 1 to 4 substituents each of which is independently (1) —$C_{1-4}$ alkyl, optionally mono-substituted with —OH, —O—$C_{1-4}$ alkyl, —O—$C_{1-4}$ haloalkyl, —CN, —N($R^aR^b$), —C(=O)N($R^aR^b$), —C(=O)$R^a$, —$CO_2R^c$, —S(O)$_n R^c$, —$SO_2$N($R^aR^b$), —N($R^a$)C(=O)$R^b$, —N($R^a$)$CO_2R^c$, —N($R^a$)$SO_2R^c$, —N($R^a$)$SO_2$N($R^aR^b$), —OC(=O)N($R^aR^b$), or —N($R^a$)C(=O)N($R^aR^b$), (2) —O—$C_{1-4}$ alkyl, optionally mono-substituted with —OH, —O—$C_{1-4}$ alkyl, —O—$C_{1-4}$ haloalkyl, —S(O)$_n R^c$, —N($R^a$)—$CO_2R^c$, —C(=O)N($R^aR^b$), —$SO_2$N($R^aR^b$), —N($R^a$)C(=O)$R^b$, —N($R^a$)$CO_2R^c$, —N($R^a$)$SO_2R^c$, —N($R^a$)$SO_2$N($R^aR^b$), —OC(=O)N($R^aR^b$), or —N($R^a$)C(=O)N($R^aR^b$), (3) —$C_{1-4}$ haloalkyl, (4) —O—$C_{1-4}$ haloalkyl, (5) —OH, (6) halo, (7) —CN, (8) —$NO_2$, (9) —N($R^aR^b$),

(10) —$SR^c$,

(11) —S(=O)$R^c$,

(12) —$SO_2R^c$,

(13) —N($R^a$)$SO_2R^c$,

(14) —$SO_2$N($R^aR^b$),

(15) —N($R^a$)C(=O)$R^b$, or

(16) —N($R^a$)$CO_2R^c$; and $R^6$ is:

(1) —O—$C_{1-6}$ alkyl, (2) —N($R^uR^v$), (3) —O—$C_{1-6}$ haloalkyl, (4) —O—$C_{1-6}$ alkyl-aryl (5) —O—$C_{1-6}$ alkyl-HetB, or (6) —O—$C_{1-6}$ alkyl-HetC, wherein $R^u$ is —H or —$C_{1-6}$ alkyl;

$R^v$ is —H, —$C_{1-6}$ alkyl, —$C_{3-6}$ cycloalkyl, or independently has the same definition as $R^1$ above;

HetB is a 5- or 6-membered saturated or mono-unsaturated ring containing from 1 to 4 heteroatoms independently selected from N, O and S, wherein the ring is optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and HetC is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or oxo.

3. The compound according to claim 2, or a pharmaceutically acceptable salt thereof, wherein in $R^1$ is —$(CH_2)_{1-4}$-phenyl, wherein the phenyl is optionally substituted with from 1 to 3 substituents each of which is independently (1) —$C_{1-4}$ alkyl, optionally mono-substituted with —OH, —O—$C_{1-4}$ alkyl, —O—$C_{1-4}$ haloalkyl, —CN, —N($R^aR^b$), —C(=O)N($R^aR^b$), —C(=O)$R^a$, —$CO_2R^c$, —S(O)$_n R^c$, or —$SO_2$N($R^aR^b$), (2) —O—$C_{1-4}$ alkyl, (3) —$C_{1-4}$ haloalkyl, (4) —O—$C_{1-4}$ haloalkyl, (5) —OH, (6) halo, (7) —CN, (8) —$NO_2$, (9) —N($R^aR^b$),

(10) —$SR^c$,

(11) —S(=O)$R^c$,

(12) —$SO_2R^c$,

(13) —N($R^a$)$SO_2R^c$,

(14) —$SO_2$N($R^aR^b$),

(15) —N($R^a$)C(=O)$R^b$, or

(16) —N($R^a$)$CO_2R^c$.

4. The compound according to claim 3, or a pharmaceutically acceptable salt thereof, wherein $R^1$ is:

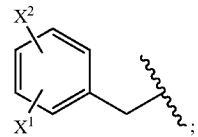

wherein $X^1$ and $X^2$ are each independently (1) —H, (2) methyl, (3) ethyl, (4) methoxy, (5) ethoxy, (6) —$CF_3$, (7) fluoro, (8) bromo, or (9) chloro.

5. The compound according to claim 4, or a pharmaceutically acceptable salt thereof, wherein $R^1$ is 4-fluorobenzyl.

6. The compound according to claim 1, or a pharmaceutically acceptable salt thereof, wherein:

$R^2$ is —H or —$C_{1-4}$ alkyl;

$R^3$ is —H or —$C_{1-4}$ alkyl;

$R^4$ is:

(1) —H, (2) —$C_{1-4}$ alkyl optionally substituted with one of —OH, —O—$C_{1-4}$ alkyl, —O—$C_{1-4}$ haloalkyl, —CN, —N($R^aR^b$), —C(=O)N($R^aR^b$), —C(=O)$R^a$, —$CO_2R^c$, —S(O)$_n R^c$, —$SO_2$N($R^aR^b$), —N($R^a$)—C($R^b$)=O, —N($R^a$)$SO_2R^b$, or —N($R^a$)$SO_2$N($R^aR^b$), (3) —C(=O)N($R^aR^b$), (4) —$R^k$, (5) —$C_{1-4}$ alkyl substituted with $R^k$, (6) —$C_{1-4}$ alkyl-O—$R^k$, or (7) —$C_{1-4}$ alkyl-O—$C_{1-4}$ alkyl-$R^k$; and $R^5$ is —H.

7. The compound according to claim 1, or a pharmaceutically acceptable salt thereof, wherein $R^6$ is:

(1) —O—$C_{1-4}$ alkyl, (2) —N($R^uR^v$), (3) —O—$C_{1-4}$ haloalkyl, (4) —O—$C_{1-4}$ alkyl-aryl (5) —O—$C_{1-4}$ alkyl-HetB, or
(6) —O—$C_{1-4}$ alkyl-HetC,
wherein
$R^u$ is —H or —$C_{1-4}$ alkyl;
$R^v$ is —H, —$C_{1-4}$ alkyl, or cyclopropyl;
HetB is a 5- or 6-membered saturated ring containing a total of from 1 to 4 heteroatoms independently selected from 1 to 4 N atoms, from 0 to 2 O atoms, and from 0 to 2 S atoms, wherein the saturated ring is optionally substituted with from 1 to 4 substituents each of which is independently halogen, —$C_{1-4}$ alkyl, —$C_{1-4}$ haloalkyl, —O—$C_{1-4}$ alkyl, —O—$C_{1-4}$ haloalkyl, or oxo; and
HetC is a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently —$C_{1-4}$ alkyl, —$C_{1-4}$ haloalkyl, —O—$C_{1-4}$ alkyl, —O—$C_{1-4}$ haloalkyl, or oxo.

8. A compound of Formula (II), or a pharmaceutically acceptable salt thereof:

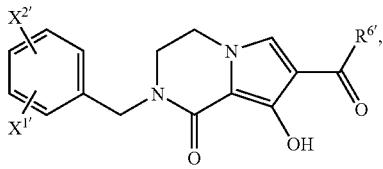

(II)

wherein:
$X^{1'}$ and $X^{2'}$ are each independently:
(1) —H,
(2) $C_{1-4}$ alkyl,
(2) —O—$C_{1-4}$ alkyl,
(3) —$C_{1-4}$ haloalkyl,
(4) —O—$C_{1-4}$ haloalkyl, or
(5) halo; and
$R^{6'}$ is:
(1) —O—$C_{1-4}$ alkyl, or
(2) —N($R^u R^v$);
wherein
$R^u$ is —H or —$C_{1-4}$ alkyl; and
$R^v$ is —$C_{1-4}$ alkyl or cyclopropyl.

9. A compound according to claim 8, or a pharmaceutically acceptable salt thereof, wherein:
wherein $X^{1'}$ and $X^{2'}$ are each independently:
(1) —H,
(2) methyl,
(2) —OCH$_3$,
(3) —CF$_3$,
(4) —OCF$_3$,
(5) chloro,
(6) fluoro, or
(7) bromo; and
$R^{6'}$ is:
(1) methoxy
(2) ethoxy, or
(3) —N($R^u R^v$);
wherein
$R^u$ is —H; and
$R^v$ is methyl, ethyl, or cyclopropyl.

10. The compound according to claim 8, which is a compound of Formula (III), or a pharmaceutically acceptable salt thereof:

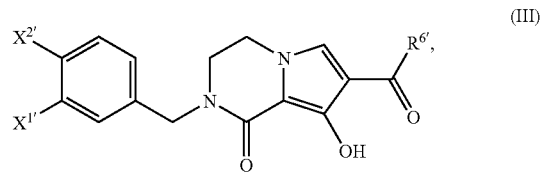

(III)

wherein $X^{1'}$ and $X^{2'}$ are each independently —H or halo.

11. The compound according to claim 10, or a pharmaceutically acceptable salt thereof, wherein
$X^{1'}$ and $X^{2'}$ are each independently —H, fluoro, chloro, or bromo; and
$R^{6'}$ is:
(1) methoxy,
(2) ethoxy, or
(3) —N($R^u R^v$);
wherein
$R^u$ is —H; and
$R^v$ is methyl, ethyl, or cyclopropyl.

12. A compound according to claim 1, or a pharmaceutically acceptable salt thereof, which is a compound of Formula (IV):

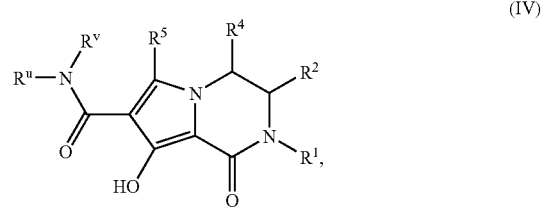

(IV)

wherein
$R^u$ is —H or —$C_{1-6}$ alkyl;
$R^v$ is $C_{1-6}$ alkyl which is substituted with 1 or 2 substituents each of which is independently:
(1) $C_{3-8}$ cycloalkyl,
(2) aryl,
(3) a 5- or 6-membered saturated or mono-unsaturated heterocyclic ring containing from 1 to 4 heteroatoms independently selected from N, O and S,
(4) a 5- or 6-membered heteroaromatic ring containing from 1 to 4 heteroatoms independently selected from N, O and S, or
(5) a 9- or 10-membered fused bicyclic heterocycle containing from 1 to 4 heteroatoms independently selected from N, O and S, wherein at least one of the rings is aromatic;
wherein
(A) each cycloalkyl is optionally substituted with from 1 to 3 substituents, each of which is independently halo, —$C_{1-6}$ alkyl, or —O—$C_{1-6}$ alkyl;
(B) each aryl is optionally substituted with from 1 to 5 substituents each of which is independently
(1) —$C_{1-6}$ alkyl, optionally substituted with from 1 to 3 substituents each of which is independently —OH, —O—$C_{1-6}$ alkyl, —O—$C_{1-6}$ haloalkyl, —CN, —NO$_2$, —N($R^a R^b$), —C(=O)N($R^a R^b$), —C(=O)$R^a$, —CO$_2 R^c$, S(O)$_n R^c$, —SO$_2$N($R^a R^b$), —N($R^a$)C(=O)$R^b$, —N($R^a$)CO$_2 R^c$, —N($R^a$)SO$_2 R^c$, —N($R^a$)SO$_2$N($R^a R^b$), —OC(=O)N($R^a R^b$), or —N($R^a$)C(=O)N($R^a R^b$), (2) —O—$C_{1-6}$ alkyl, optionally substituted with from 1 to 3 substituents each of which is independently —OH, —O—$C_{1-6}$ alkyl, —O—$C_{1-6}$ haloalkyl, —S(O)$_n$R$^c$, —C(=O)N(R$^a$R$^b$), —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$), (3) —$C_{1-6}$ haloalkyl,
(4) —O—$C_{1-6}$ haloalkyl,
(5) —OH,
(6) halo,
(7) —CN,
(8) —NO$_2$,
(9) —N(R$^a$R$^b$),
(10) —C(=O)N(R$^a$R$^b$),
(11) —C(=O)R$^a$,
(12) —CO$_2$R$^c$,
(13) —SR$^c$,
(14) —S(=O)R$^c$,
(15) —SO$_2$R$^c$,
(16) —N(R$^a$)SO$_2$R$^c$,
(17) —SO$_2$N(R$^a$R$^b$),
(18) —N(R$^a$)C(=O)R$^b$, or
(19) —N(R$^a$)CO$_2$R$^c$;

(C) each saturated or mono-unsaturated heterocyclic ring is
(i) optionally substituted with from 1 to 5 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
(ii) optionally substituted with 1 or 2 substituents each of which is independently aryl or a 5- or 6-membered heteroaromatic ring containing from 1 to 4 heteroatoms independently selected from N, O and S; and (D) each heteroaromatic ring or each fused bicyclic heterocycle is
(i) optionally substituted with from 1 to 7 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; and
(ii) optionally substituted with 1 or 2 substituents each of which is independently aryl or —$C_{1-6}$ alkyl-aryl; and R$^1$ is —H or —$C_{1-6}$ alkyl.

13. The compound according to claim 12, or a pharmaceutically acceptable salt thereof, wherein R$^v$ is —$C_{1-4}$ alkyl mono-substituted with aryl; wherein the aryl is optionally substituted with from 1 to 4 substituents each of which is independently
(1) —$C_{1-4}$ alkyl, optionally mono-substituted with —OH, —O—$C_{1-4}$ alkyl, —O—$C_{1-4}$ haloalkyl, —CN, —N(R$^a$R$^b$), —C(=O)N(R$^a$R$^b$), —C(=O)R$^a$, —CO$_2$R$^c$, —S(O)$_n$R$^c$, —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
(2) —O—$C_{1-4}$ alkyl, optionally mono-substituted with —OH, —O—$C_{1-4}$ alkyl, —O—$C_{1-4}$ haloalkyl, —S(O)$_n$R$^c$, —N(R$^a$)—CO$_2$R$^c$, —C(=O)N(R$^a$R$^b$), —SO$_2$N(R$^a$R$^b$), —N(R$^a$)C(=O)R$^b$, —N(R$^a$)CO$_2$R$^c$, —N(R$^a$)SO$_2$R$^c$, —N(R$^a$)SO$_2$N(R$^a$R$^b$), —OC(=O)N(R$^a$R$^b$), or —N(R$^a$)C(=O)N(R$^a$R$^b$),
(3) —$C_{1-4}$ haloalkyl,
(4) —O—$C_{1-4}$ haloalkyl,
(5) —OH,
(6) halo,
(7) —CN,
(8) —NO$_2$,
(9) —N(R$^a$R$^b$),
(10) —SR$^c$,
(11) —S(=O)R$^c$,
(12) —SO$_2$R$^c$,
(13) —N(R$^a$)SO$_2$R$^c$,
(14) —SO$_2$N(R$^a$R$^b$),
(15) —N(R$^a$)C(=O)R$^b$, or
(16) —N(R$^a$)CO$_2$R$^c$.

14. The compound according to claim 13, or a pharmaceutically acceptable salt thereof, wherein R$^v$ is:

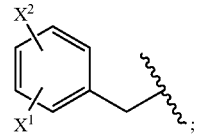

wherein X$^1$ and X$^2$ are each independently
(1) —H,
(2) methyl,
(3) ethyl,
(4) methoxy,
(5) ethoxy,
(6) —CF$_3$,
(7) fluoro,
(8) bromo, or
(9) chloro.

15. The compound according to claim 14, or a pharmaceutically acceptable salt thereof, wherein R$^v$ is 4-fluorobenzyl.

16. The compound according to claim 12, or a pharmaceutically acceptable salt thereof, wherein:
R$^u$ is —H;
R$^5$ is —H;
R$^4$ is:
(1) —H,
(2) —$C_{1-4}$ alkyl optionally substituted with one of —OH, —N(R$^a$R$^b$), or —C(=O)N(R$^a$R$^b$),
(3) —C(=O)N(R$^a$R$^b$),
(4) —(CH$_2$)$_{1-3}$—R$^k$,
(5) —(CH$_2$)$_{1-3}$—O—R$^k$, or
(6) —(CH$_2$)$_{1-3}$—O—(CH$_2$)$_{1-3}$—R$^k$;
R$^2$ is —H; and
R$^1$ is —$C_{1-4}$ alkyl.

17. A compound selected from the group consisting of:

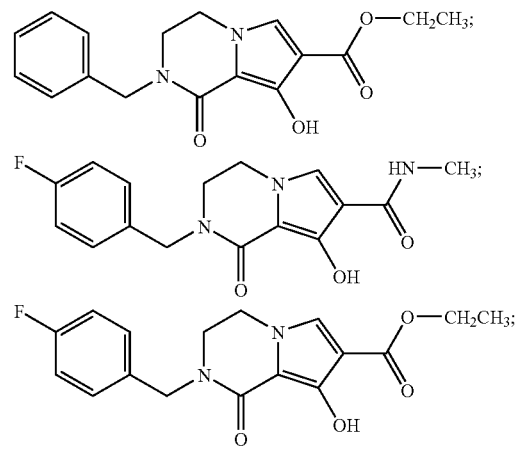

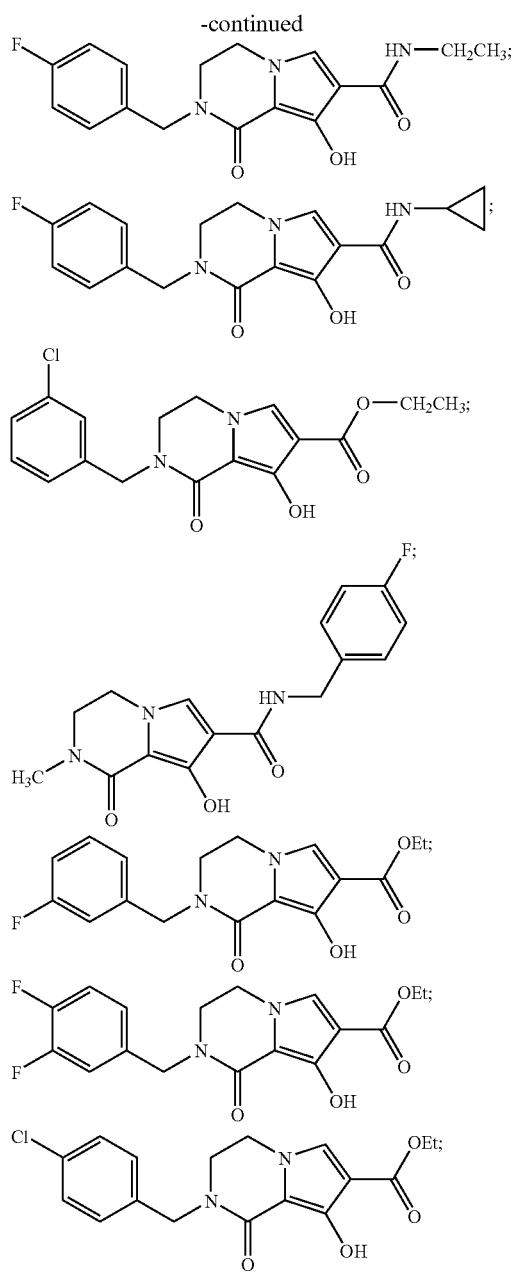

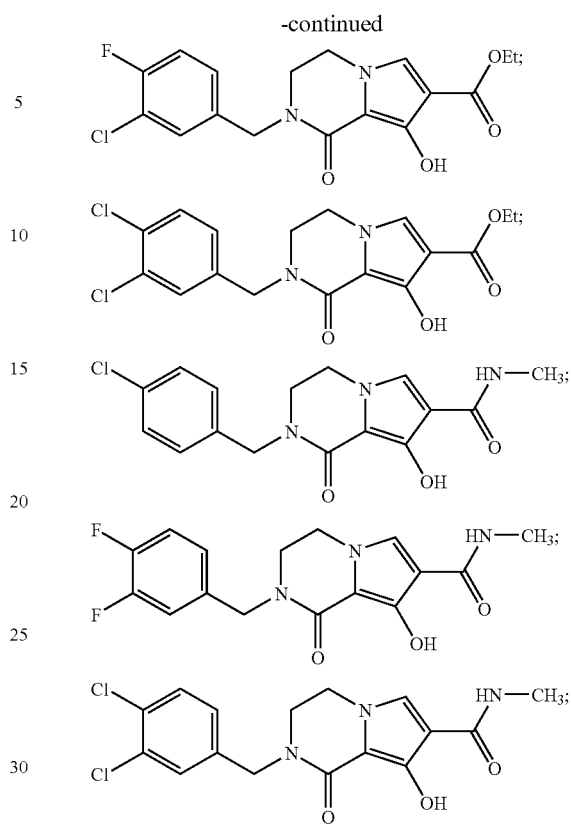

and pharmaceutically acceptable salts thereof.

18. A pharmaceutical composition comprising a therapeutically effective amount of a compound according to claim 1, or a pharmaceutically acceptable salt thereof, and a pharmaceutically acceptable carrier.

19. A method for treating infection by HIV-1 or for treating or delaying the onset of AIDS due to HIV-1 in a subject in need thereof which comprises administering to the subject a therapeutically effective amount of the compound according to claim 1, or a pharmaceutically acceptable salt thereof.

\* \* \* \* \*